US011001830B2

(12) United States Patent
Lorenz et al.

(10) Patent No.: US 11,001,830 B2
(45) Date of Patent: May 11, 2021

(54) METHOD OF DETECTING NEW IMMUNOGENIC T CELL EPITOPES AND ISOLATING NEW ANTIGEN-SPECIFIC T CELL RECEPTORS BY MEANS OF AN MHC CELL LIBRARY

(71) Applicants: MAX-DELBRÜCK-CENTRUM FÜR MOLEKULARE MEDIZIN IN DER HELMHOLTZ-GEMEINSCHAFT, Berlin (DE); HELMHOLTZ ZENTRUM MÜNCHEN-DEUTSCHES FORSCHUNGSZENTRUM FÜR GESUNDHEIT UND UMWELT, Neuherberg (DE)

(72) Inventors: Felix Lorenz, Berlin (DE); Wolfgang Uckert, Berlin (DE); Christian Ellinger, Munich (DE); Dolores Schendel, Munich (DE)

(73) Assignees: MAX-DELBRÜCK-CENTRUM FÜR MOLEKULARE MEDIZIN IN DER HELMHOLTZ-GEMEINSCHAFT, Berlin (DE); HELMHOLTZ ZENTRUM MÜNCHEN-DEUTSCHES FORSCHUNGSZENTRUM FÜR GESUNDHEIT UND, Neuherberg (DE)

( * ) Notice: Subject to any disclaimer, the term of this patent is extended or adjusted under 35 U.S.C. 154(b) by 421 days.

(21) Appl. No.: 15/558,765

(22) PCT Filed: Mar. 15, 2016

(86) PCT No.: PCT/EP2016/055518
§ 371 (c)(1),
(2) Date: Sep. 15, 2017

(87) PCT Pub. No.: WO2016/146618
PCT Pub. Date: Sep. 22, 2016

(65) Prior Publication Data
US 2018/0073013 A1 Mar. 15, 2018

(30) Foreign Application Priority Data
Mar. 16, 2015 (EP) .................................... 15159212

(51) Int. Cl.
*C12N 15/10* (2006.01)
*C07K 14/725* (2006.01)
*C07K 14/005* (2006.01)

(52) U.S. Cl.
CPC ........ *C12N 15/1037* (2013.01); *C07K 14/005* (2013.01); *C07K 14/7051* (2013.01); *C12N 2710/16122* (2013.01); *C12N 2710/16134* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS 7,026,443 B1  4/2006  Sette et al.

FOREIGN PATENT DOCUMENTS

| JP | 2009-502185 A | 1/2009 | |
| JP | 2013-176390 A | 9/2013 | |
| WO | 2004/011650 A2 | 2/2004 | |
| WO | 2004011650 | 2/2004 | |
| WO | 2011024482 A1 | 3/2011 | |
| WO | WO-2012038055 A1 * | 3/2012 | ......... C07K 14/4748 |
| WO | 2012/044999 A2 | 4/2012 | |

(Continued)

OTHER PUBLICATIONS

Spranger et al. (Blood. 2012;119(15):3440-3449). (Year: 2012).*
Simon et al. (Cancer Immunol Res; 2(12); 1230-44 (2014)). (Year: 2014).*
International Search Report and Written Opinion, issued by the International Searching Authority in Application No. PCT/EP2016/055518, dated Jun. 9, 2016.
Restifo, et al., "Adoptive immunotherapy for cancer: harnessing the T cell response", Nature Reviews Immunology, vol. 12, No. 4, Apr. 1, 2012, pp. 269-281.

(Continued)

*Primary Examiner* — Zachary S Skelding
(74) *Attorney, Agent, or Firm* — Meunier Carlin & Curfman LLC

(57) ABSTRACT

The present invention relates to the field of immunotherapy, in particular, to adoptive T cell therapy, T cell receptor (TCR) gene therapy and vaccination. The invention provides a method for preparing a nucleic acid encoding the TCR alpha chain construct (TRA) and TCR beta chain construct (TRB) of a TCR construct specific for an epitope from an antigen presented on major histocompatibility complex (MHC), comprising contacting T cells isolated from a donor with a library of artificial antigen presenting cells (APC) comprising cells expressing all MHC I or MHC II alleles present in the donor, preferably, in K562 cells. The TCR construct can be expressed in a T cell, which is useful for adoptive T cell therapy, e.g., of cancer, viral infections or autoimmune diseases. The invention further provides a method for identifying the epitope recognized by said TCR. Immunogenic epitopes recognized by said TCRs can be used to develop vaccine formulations to induce antigen-specific T cell immunity in patients. The invention further provides pairs of two TCR constructs and respective immunogenic epitopes obtained by the method of the invention, wherein the epitopes are from human papillomavirus (HPV) 16 (also designated alphapapillomavirus 9) oncoprotein E5 and human cytomegalovirus (CMV) protein pp65.

Figure 1:
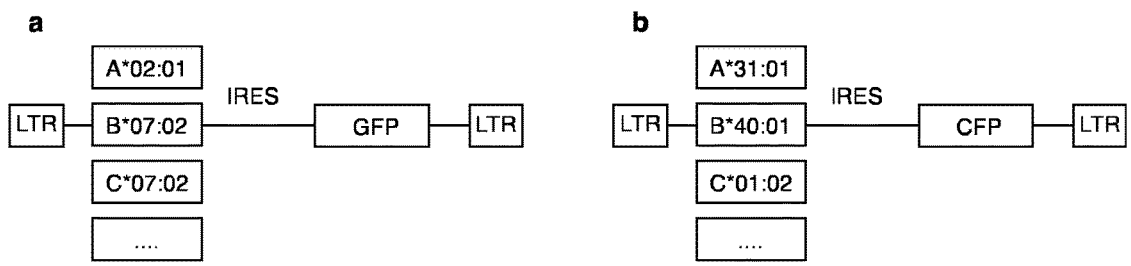

7 Claims, 5 Drawing Sheets
Specification includes a Sequence Listing.

(56) References Cited

FOREIGN PATENT DOCUMENTS

| | | |
|---|---|---|
| WO | 2012044999 | 4/2012 |
| WO | 2016138122 A1 | 9/2016 |

OTHER PUBLICATIONS

Chen, et al., "Cytotoxic-T-lymphocyte human papillomavirus type 16 E5 peptide with CpG-oligodeoxynucleotide can eliminate tumor growth in C57BL/6 mice", Journal of Virology, The American Society for Microbiology, US, vol. 78, No. 3, Feb. 1, 2004, pp. 1333-1343.
Boucherma, et al., "HLA-A*01:03, HLA-A*24:02, HLA-B*08:01, HLA-B*27:05, HLA-B*35:01, HLA-B*44:02, and HLA-C*07:01 Monochain Transgenic/H-2 Class I Null Mice: Novel Versatile Preclinical Models of Human T Cell Response", The Journal of Immunology, The American Association of Immunologists, US, vol. 191, No. 2, Jul. 15, 2013, pp. 583-593.
Database XP-002744178.
Database XP-002744177.
Lozzio, et al., "Human chronic myelogenous leukemia cell-line with positive Philadelphia chrosmosome", Blood, vol. 45, No. 3, 1975, pp. 321-334.
Klein, et al., "Properties of the k562 Cell Line, Derived From a Patient With Chronic Myeloid Leikemia", Int. J. Cancer, 18, 421-431 (1976).
Drew, et al., "Group-specific human granulocyte antigens on a chronic myelogenous leukemia cell line with a Philadelphia chromosome marker", Blood, vol. 49, No. 5, 1977 pp. 715-718.
Halbert, et al., "Identification of the E5 open reading frame of human papillomavirus type 16", Journal of Virology, 1988, 62(3):1071.
Reusser, et al., "Cytotoxic T-Lymphocyte Response to Cytomegalovirus after human allogeneic bone marrow transplantation: pattern of recovery and correlation with cytomegalovirus infection and disease", Blood, vol. 78, No. 5, 1991, pp. 1373-1380.
Straight, et al., "The E5 oncoprotein of human papillomavirus type 16 transforms fibroblasts and effects the downregulation of the epidermal growth factor receptor in keratinocytes", Journal of Virology, Vo. 67, No. 8, 1993, pp. 4521-4532.
Baum, et al., "Novel Retroviral vectors for efficient expression of the multidrug resistance (mdr-1) gene in early hematopoietic cells", Journal of Virology, vol. 69, No. 12, 1995, pp. 7541-7547.
Manz, et al., "Analysis and sorting of live cells according to secreted molecules, relocated to a cell-surface affinity matrix", Proc. Natl. Acad. Sci. USA, vol. 92, pp. 1921-1925, 1995.
Altman, et al., "Phenotypic analysis of antigen-specific T Lymphocytes", Science, New Series, vol. 274, No. 5284, 1996, pp. 94-96.
Bai, et al., "Quantitative polymerase chain reaction for human herpesvirus diagnosis and measurement of Epstein-Barr virus burden in posttransplant lymphoproliferative disorder", Clinical Chemistry, 43:10, pp. 1843-1849, 1997.
Pascolo, et al., "HLA-A2.1-restricted education and cytolytic activity of CD8+ T Lymphocytes from β2 Microglobulin (β2m double knockout mice", J. Exp. Med., vol. 185, No. 12, 1997, pp. 2043-2051.
Iezzi, et al., "The duration of antigenic stimulation determines the fate of naïve and effector T cells", Immunity, vol. 8, 89-95, 1998.
Brosterhus, et al., "Enrichment and detection of live antigen-specific CD4+ and CD8+ T cells based on cytokine secretion", Eur. J. Immunol 1999, 29, pp. 4053-4059.
Walboomers, et al., "Human papillomavirus is an necessary cause of invasive cervical cancer worldwide", Journal of Pathology, 189: 12-19, 1999.
Latouche et al., "Induction of human cytotoxic T lymphocytes by artificial antigen-presenting cells", Nature Biotechnology, vol. 18, 2000, pp. 405-409.
Schambach, et al., Context dependence of different modules for posttranscriptional enhancement of gene expression from retroviral vectors, Molecular Therapy, vol. 2, No. 5, 2000, pp. 435-445.
Becker, et al., "Adoptive tumor therapy with T lymphocytes enriched through an IFN-γ capture assay", Nature Medicine, vol. 7, No. 10, 2001, pp. 1159-1162.
Chang, et al., The Expression of HPV-16 E5 protein in squamous neoplastic changes in the uterine cervix, J Biomed Sci 2001, 8:206-213.
Britten, et al., "The use of HLA-A*0201-transfected K562 as standard antigen-presenting cells for CD8+ T lymphocytes in IFN-γ ELISPOT assays", Journal of Immunological Methods 259 (2002) 95-110.
Einsele, et al., "Infusion of cytomegalovirus(CMV)-specific T cells for the treatment of CMV infection not responding to antiviral chemotherapy", Blood, 2002, vol. 99, No. 11, pp. 3916-3922.
Khan, et al., "Cytomegalovirus seropositivity drives the CD8 T Cell repertoire toward greater clonality in healthy elderly individuals", J. Immunol 2002; 169:1984-1992.
Knabel, et al., "Reversible MHC multimer staining for functional isolation of T-cell populations and effective adoptive transfer", Nature Medicine, vol. 8, No. 6, 2002, pp. 631-637.
Reddehase, Matthias J., "Antigens and immunoevasins: opponents in cytomegalovirus immune surveillance", Nature Reviews, vol. 2, 2002, pp. 831-844.
Schumacher, Ton N. M., "T-cell-receptor gene therapy", Nature 2002, vol. 2, pp. 512-519.
Zur Hausen, Harald, "Papillomaviruses and cancer: from basic studies to clinical application", Nature 2002, vol. 2, pp. 342-350.
Engels, et al., "Retroviral vectors for high-level transgene expression in T lymphocytes", Human Gene Therapy 14:1155-1168, 2003.
Bakker, et al., "MHC multimer technology: current status and future prospects", Current Opinion in Immunology 2005m 17: 428-433.
Cohen, et al., "Enhanced antitumor activity of murine-human hybrid T-cell receptor (TCR) in human lymphocytes is associated with improved pairing and TCR/CD3 stability", Cancer Res 2006, 66:8878-8886.
Ho, et al., "In vitro methods for generating CD8+ T-cell clones for immunotherapy from the naïve repertoire", Journal of Immunological Methods 310 2006, pp. 40-52.
Cohen, et al., "Enhanced antitumor activity of T cells engineered to express T-cell receptors with a second disulfide bond", Cancer Res 2007; 67: (8), pp. 3898-3903.
Kuball, et al., "Facilitating matched pairing and expression of TCR chains introduced into human T cells", Blood, 2007, vol. 109, No. 6, pp. 2331-2338.
Suhoski, et al., "Engineering artificial antigen-presenting cells to express a diverse array of co-stimulatory molecules", Molecular Therapy, 2007, vol. 15, No. 5, pp. 981-988.
Wolfl, et al., "Activation-induced expression of CD137 permits detection, isolation, and expansion of the full repertoire of CD8+ T cells responding to antigen without requiring knowledge of epitope specificities", Blood 2007, 110: 201-210.
Woodman, et al., "The natural history of cervical HPV infection: unresolved issues", Nature Reviews, vol. 7, 2007, pp. 11-22.
Chervin, et al., "Engineering higher affinity T cell receptors using a T cell display system", Journal of Immunological Methods 339(2008) 175-184.
Leisegang, et al., "Enhanced functionality of T cell receptor-redirected T cells is defined by the transgene cassette", J Mol Med 2008 86:573-583.
Melief, Cornelis J.M., "Cancer Immunotherapy by dendritic cells", Immunity 29, 2008 pp. 372-383.
Robbins, et al., "Single and dual amino acid substitutions in TCR CDRs can enhance antigen-specific T cell functions", J of Immunology 2008; 180; 6116-6131.
Watanabe, et al., "CD137-guided isolation and expansion of antigen-specific CD8 cells for potential use in adoptive immunotherapy".
Wölfl, et al., "Use of CD137 to study the full repertoire of CD8+ T cells without the need to know epitope specificities", Cytometry A, 2008; 73(11): 1043-1049.
Fontana, et al., "Peripheral blood lymphocytes genetically modified to express the self/tumor antigen MAGE-A3 induce antitumor immune responses in cancer patients", Blood, 2009, vol. 113, No. 8, pp. 1651-1660.

(56) References Cited

OTHER PUBLICATIONS

Hadrup, et al., "Parallel detection of antigen-specific T-cell responses by multidimensional encoding of MHC multimers", Nature Methods, vol. 6, No. 7, 20096, pp. 520-528.
Hasan, et al., "A panel of artificial APCs expressing prevalent HLA alleles permits generation of cytotoxic T cells specific for both dominant and subdominant viral epitopes for adoptive therapy", J Immunol 2009; 183:2837-2850.
Kenter, et al, "Vaccination against HPV-16 oncoproteins for vulvar intraepithelial neoplasia", N Engl J Med 2009; 361:1838-1847.
Wilde, et al., "Dendritic cells pulsed with RNA encoding allogeneic MHC and antigen induce T cells with superior antitumor activity and higher TCR functional avidity", Blood 2009; 114:2131-2139.
Bürdek, et al., "Three-day dendritic cells for vaccine development: Antigen uptake, processing and presentation", Journal of Translational Medicine 2010, 8:90.
Butler, et al., "A panel of human cell-based artificial APC enables the expansion of long-lived antigen-specific CD4$^+$ T cells restricted by prevalent HLA-DR alleles", International Immunology, vol. 22, No. 11, pp. 863-873.
Li, et al., "Transgenic mice with a diverse human T cell antigen receptor repertoire", Nature Medicine, 2010 vol. 16, No. 9, 1029-1035.
Moody, et al., "Human papillomavirus oncoproteins: pathways to transformation", Nature 2010, vol. 10, pp. 550-560.
Schmitt, et al., "Diagnosing cervical cancer and high-grade precursors by HPV16 transcription patters", Cancer Res 2010; 70:249-256.
Sommermeyer, et al., "Minimal amino acid exchange in human TCR constant regions fosters improved function of TCR gene-modified T cells", J Immunol 2010; 184; 6223-6231.
Spranger, et al, "Generation of Th1-polarizing dendritic cells using the TLR7/8 agonist CL075", J Immunol 2010; 185:738-747.
Davis, et al., "Interrogating the repertoire: broadening the scope of peptide-MHC multimer analysis", Nature Reviews, 2011, vol. 11, pp. 551-558.
Gonzalez-Galarza, et al., "Allele frequency net: a database and online repository for immune gene frequencies in worldwide populations", Nucleic Acids Research, 2011, vol. 39, D913-D919.
Lamers, et al., "Immune responses to transgene and retroviral vector in patients treated with ex vivo-engineered T cells", Blood 2011; vol. 117, No. 1, pp. 72-82.
Ghazi, et al., "Generation of polyclonal CMV-specific T cells for the adoptive immunotherapy of glioblastoma", J Immunother 2012; 35(2):159-168.
Liddy, et al., "Monoclonal TCR-redirected tumor cell killing", Nature Medicine, 2012; vol. 18, No. 6, pp. 980-988.
Restifo, et al., "Adoptive immunotherapy for cancer: harnessing the T cell response", Nature Reviews 2012; vol. 12, pp. 269-281.
Spranger, et al., "TCR-transgenic lymphocytes specific for HMMR/Rhamm limit tumor outgrowth in vivo", Blood 2012:119:3440-3449.
Stern, et al., "Therapy of Human Papillomavirus-related disease", Vaccine 305, 2012, F71-F82.
Anderson, et al., "Impaired tumor antigen processing by immunoproteasome-expressing CD40-activated B cells and dendritic cells", Cancer Immunol Immunother 2011; 60(6):857-867.
Dössinger, et al., "MHC multimer-guided and cell culture-independent isolation of functional T cell receptors from single cells facilitates TCR identification for immunotherapy", PLOS One 2013, vol. 8, Issue 4.
Linette, et al., "Cardiovascular toxicity and titin cross-reactivity of affinity-enhanced T cells in myeloma and melanoma", Blood 2013; 122(6):863-871.

Linnemann, et al., "High-throughput identification of antigen-specific TCRs by TCR gene capture", Nature Medicine 2013; vol. 19, No. 11 pp. 1534-1543.
McKinney, et al., "A strategy to determine HLA class II restriction broadly covering the DR, DP, and DQ allelic variants most commonly expressed in the general population", Immunogenetics 2013; 65:357-370.
Söderberg-Nauclér, et al., "Survival in patients with glioblastoma receiving valganciclovir", N Engl J Med 2013; 369; 10.
Tang, et al., "The landscape of viral expression and host gene fusion and adaptation in human cancer", Nature Communications 4:2513.
Boegel, et al., "A catalog of HLA type, HLA expression, and neo-epitope candidates in human cancer cell lines", OncoImmunology, vol. 3, Issue 8.
Han, et al., "Linking T-cell receptor sequence to functional phenotype at the single-cell level", Nature Biotechnology 2014.
Hinrichs, et al., "Exploiting the curative potential of adoptive T-cell therapy for cancer", Immunological Reviews 2014; vol. 257:56-71.
Schuessler, et al., "Autologous T-cell therapy for cytomegalovirus as a consolidative treatment for recurrent glioblastoma", Cancer Res 2014; 74(13) pp. 3466-3476.
Vonderheide, et al., "Engineering T cells for cancer: our synthetic future", Immunological Reviews 2014; vol. 257:7-13.
Wick, et al., "CMV infection and glioma, a highly controversial concept struggling in the clinical arena", Neuro-Oncology 2014; 16(3), 332-333.
Yee, Cassian, "The use of endogenous T cells for adoptive transfer", Immunological Reviews 2014; vol. 257:250-263.
Zeng, et al., "Artificial antigen-presenting cells expressing CD80, CD70, and 4-1BB ligand efficiently expand functional T cells specific to tumor-associated antigens", Immunobiology 2014; 219; 583-592.
Examination Report issued by the Australian Government in Application No. 2016232280, dated Dec. 14, 2017.
Examination Report issued by the European Patent Office in Application No. 16713750.4, dated Jul. 9, 2018 (6 pages).
Database Geneseq [Online], "MHC class I/antigenic peptide to generate reversible multimer Seq ID: 154", May 24, 2012, 2 pages.
Database Geneseq [Online], "Human papillomavirus peptide #770", May 6, 2004, 1 page.
Restifo, N.P. et al. "Adoptive immunotherapy for cancer: harnessing the T cell response" Nature Reviews, vol. 12, No. 4, Apr. 1, 2012, pp. 269-281.
Chen, Y. et al. "Cytotoxic-T-Lymphocyte Human Pappilomavirus Type 16 E5 Peptide with CpG-Oligodeoxynucleotide Can Eliminate Tumor Growth in C57BL/6 Mice", Journal of Virology, vol. 78, No. 3, Feb. 2004, pp. 1333-1343.
Zeng, W. et al. "Artifical antigen-presenting cells expressing CD80, CD70, and 4-1BB ligand efficiently expand functional T cells specific to tumor-associated antigens", Immunobiology, vol. 219, No. 8, Mar. 20, 2014, pp. 583-592.
Boucherma, R. et al. "HLA-A*01:03, HLA-A*24:02, HLA-B*08:01, HLA-B*27:05, HLA-B*35:01, HLA-B*44:02, and HLA-C*07:01 Monochain Transgenic/H-2 Class I Null Mice: Novel Versatile Preclinical Models of Human T Cell Responses", The Journal of Immunology, vol. 191, No. 2, Jul. 15, 2013, pp. 583-593.
International Search Report dated Jun. 9, 2016, from International Application No. PCT/EP2016/055518, 7 pages.
Written Opinon dated Jun. 9, 2016, from International Application No. PCT/EP2016/055518, 8 pages.
Weeks et al. "The Memory Cytotoxic T-Lymphocyte (CTL) Response to Human Cytomegalovirus Infection Contains Individual Peptide-Specific CTL Clones That Have Undergone Extensive Expansion In Vivo", Journal of Virology, 1999.

* cited by examiner

METHOD OF DETECTING NEW IMMUNOGENIC T CELL EPITOPES AND ISOLATING NEW ANTIGEN-SPECIFIC T CELL RECEPTORS BY MEANS OF AN MHC CELL LIBRARY

The present invention relates to the field of immunotherapy, in particular, to adoptive T cell therapy, T cell receptor (TCR) gene therapy and vaccination. The invention provides a method for preparing a nucleic acid encoding the TCR alpha chain construct (TRA) and TCR beta chain construct (TRB) of a TCR construct specific for an epitope from an antigen presented on major histocompatibility complex (MHC), comprising contacting T cells isolated from a donor with a library of artificial antigen presenting cells (APC) comprising cells expressing all MHC I or MHC II alleles present in the donor, preferably, in K562 cells. The TCR construct can be expressed in a T cell, which is useful for adoptive T cell therapy, e.g., of cancer, viral infections or autoimmune diseases. The invention further provides a method for identifying the epitope recognized by said TCR immunogenic epitopes recognized by said TCRs can be used to develop vaccine formulations to induce antigen-specific T cell immunity in patients. The invention further provides pairs of two TCR constructs and respective immunogenic epitopes obtained by the method of the invention, wherein the epitopes are from human papillomavirus (HPV) 16 (also designated alphapapillomavirus 9) oncoprotein E5 and human cytomegalovirus (CMV) protein pp65.

T cell receptor (TCR) gene therapy is a promising immunotherapeutic strategy to treat a variety of virus- and cancer-related indications. One key obstacle is the lack of availability of potent TCRs to be analyzed in preclinical and clinical settings. Current methods to detect and isolate antigen-specific TCRs have technical limitations, are restricted to certain MHCs or require prior knowledge of the antigenic epitope. Choice of target antigen is another key factor for the success of immunotherapies. Targeting antigens, which are specifically expressed in tumor tissue but not in normal tissue, are of particular interest.

Adoptive T cell therapies are based on the ex vivo activation and expansion of T cells to generate antigen-specific effector T cells for reinfusion into the patient (1). This process may be accompanied by genetic modification of T cells with new antigen receptors. Rapid ex vivo expansion protocols enable the generation of high numbers of T cells to break immune suppressive barriers of the tumor microenvironment to clear target cells. Overcoming immune suppressive barriers may lead to the uptake of lysed tumor cells by APCs and the presentation of further antigens—a process called epitope spreading. This may be followed by de novo priming of autologous T cells and reactivation of anergic T cells amplifying the antitumor immune response, which was induced by the adoptive T cell therapy. Adoptive T cell therapies using genetically unmodified as well as antigen receptor-engineered T cells have been used successfully to treat cancer and virus-associated diseases, refractory to other treatments (2).

A second strategy to provide T cell immunity to a patient is the application of a vaccine. Vaccines provide acquired immunity to particular pathogens or cancers and market introduction of many vaccines have led to impressive declines in morbidity and mortality caused by numerous life-threatening diseases. For the development of novel prophylactic and therapeutic vaccines it is a prerequisite to identify antigens, epitopes and MHC restriction elements, which induce T cell responses that can provide protection from and clearance of pathogenic cells expressing such antigens. Identification of antigenic epitopes, which are endogenously processed and presented by pathogenic cells and which are recognized by antigen-specific TCRs enables the development of novel vaccine formulations to induce antigen-specific immunity.

In the following, current methods to identify and isolate antigen-specific TCRs and to identify antigenic epitopes, which induce T cell responses, are reviewed.

Peripheral blood mononuclear cells (PBMCs) are the primary source of T cells for in vitro analysis. For screening, large amounts of T cells can be isolated readily from PBMCs of patient or healthy donor blood. In comparison, T cells isolated from tumor-infiltrating lymphocytes (TILs) are available in limited amounts from tumor biopsies. Biopsies can only be obtained from solid tumors (3,4). Direct sequence analysis of TCRs from PBMCs or TILs can generate massive data on TCR sequences. Prediction of TCR specificity and antigen recognition from these data sets remains impossible (5). To isolate TCRs with desired specificity from T cell samples, it is necessary to introduce an antigen-specific enrichment step before analyzing TCR sequences. Additionally, it is useful to perform functional assays to confirm antigen specificity of T cells before TCR isolation (6). Standard approaches to enrich T cells are based on antigen-specific in vitro stimulation to expand specific T cells in culture. One strategy of in vitro stimulation of antigen-specific T cells is the addition of peptides to the T cell culture, which bind to MHC I molecules. Cells in culture present the peptides to each other and antigen-specific CD8$^+$ T cells grow out. However, peptide stimulations, which is often performed at non-physiological concentrations, may lead to overstimulation and activation-induced cell death of T cells harboring high affinity TCRs to peptide/MHC (pMHC) I (7). Additionally, knowledge of epitope sequence, processing properties and MHC I binding restriction is required. Furthermore, presence of peptide-specific T cells within PBMC or TIL samples is necessary. Thus, screening for peptide-specific T cells with low precursor frequency may be limited and precludes identification of novel immunogenic antigen-MHC I combinations. Functional testing of T cells for antigen-specificity and MHC restriction is usually carried out with single T cell clones. After expansion and enrichment, single T cell clones can be grown to sufficient amounts. One factor, which must be taken into account when applying T cell cultures, is the influence of long-term cultivation conditions on resulting T cells (8). Growth capacity of T cells with a more differentiated phenotype (Tem and Teff) is limited and restricts in vitro expansion. Long-term cultivation might lead to the loss of potent TCRs of T cell clones, which have already encountered pMHC I in vivo and undergone expansion and differentiation in the donor. Thus long-term T cell cultures may introduce a bias in favoring outgrowth of undifferentiated T cells with high expansion capacity.

Detection and sorting of antigen-specific T cells is a critical step for the isolation of novel antigen-specific TCRs. The huge repertoire of TCRs with distinct specificities for pMHC led to the development of soluble MHC multimers as reagents to stain T cells specific for a known pMHC (9-11). Multimers are used for sorting of antigen-specific T cells. Multimers enable direct staining of T cells specific for the desired pMHC (12,13). However, prior knowledge of MHC restriction and peptide specificity is required to screen antigen-specific T cells within a sample. Use of multimers may rely on in silico prediction of T cell epitopes and thus harbors the risk to isolate TCRs specific for epitopes, which are not endogenously processed and presented. Additionally, T cells are selected upon their capability to bind multimer, but not necessarily upon binding to a pMHC complex at the cell surface. Multimers are custom-made reagents, which are not readily available to screen sets of different pMHCs.

In 1997, the groups of Lemonnier and Pérarnau reported the generation of a transgenic mouse stably expressing a single-chain construct of the human HLA-A*02:01 molecule fused to ß-2 microglobulin (b-2m) (HHD). Additionally, mice were knockout for murine MHC I genes. Thus, immunization results in antigen-specific T cells exclusively restricted to HHD (14). HLA-transgenic mice have since provided a novel source of antigen-specific T cells (15). Human antigens and epitopes, which are not similar in their sequence to murine counterparts, can be used for vaccination of HLA-transgenic mice to elicit antigen-specific T cell responses in the non-tolerant repertoire, because mouse T cells were not deleted in the thymus and recognize human antigens as foreign. HLA-transgenic mice provide a source of high affinity TCRs recognizing self- or similar-to-self-antigens, which have been deleted in the human repertoire due to thymic selection. Technological advances were made, when based on the HHD mouse model the first transgenic mouse was generated carrying the human TCR repertoire while in parallel the murine TCR locus was knocked out (16). However, potential problems using MHC-transgenic and/or TCR locus-transgenic mice may emerge, e.g., it is difficult to predict whether or not mouse and human thymus selection follows the same rules. Transgenic MHC molecules are artificial single-chain constructs, which may introduce a bias to selecting TCRs functionally restricted to single-chain MHCs but not native MHC I complex. Immunization of single MHC-transgenic mice does not reflect a natural immune response with a choice of six cognate MHC:I complexes. It is likely that antigens exist, which do not contain e.g. HLA-A*02:01 epitopes. Furthermore, mice carrying the human TCR locus lack few TCRs chains, which may be crucial for targeting certain pMHC I (16). In contrast, immunization of mice carrying the murine TCR locus will result in the isolation of murine TCR sequences, which may be prone to rejection when transferred into humans (17,18). An important economical factor is the infrastructure necessary to work with murine models, which is very resource-intensive with regard to costs, regulatory requirements and manpower.

Successful TCR gene therapy is dependent on the availability of novel TCRs with exquisite specificity profiles. In light of this, the present inventors addressed the need to provide a novel method to identify and isolate novel antigen-specific TCRs, and to define epitope specificity and MHC restriction of these TCRs. For the development of novel vaccines, which induce antigen-specific T cell responses, there is a need for defining novel immunogenic epitopes, which can be targeted by T cells.

This problem is solved by the present invention, in particular, by the subject matter of the claims.

The present invention provides a method for preparing a nucleic acid encoding the TCR alpha chain construct (TRA) and TCR beta chain construct (TRB) of a TCR construct specific for an epitope from a defined antigen presented on an MHC, comprising:

(a) stimulating T cells isolated from a donor with professional antigen presenting cells (APCs) presenting epitopes of said defined antigen, to enrich antigen-specific T cells; and
(b) contacting said T cells with a library of cells, wherein each cell expresses a single MHC allele, wherein the library comprises cells expressing all MHC I or MHC II alleles present in the donor, and wherein the cells of said library present epitopes of said defined antigen; and
(c) selecting T cells activated by said contact, preferably, based on an activation marker expressed by said activated T cells; and
(d) isolating the nucleic acids encoding the TCR alpha and TCR beta chain of the TCR of said T cells.

In the context of the present invention "a" does not exclusively refer to "one", but also encompasses "two or more". For example, the method of the present invention can be used to prepare one or more, e.g., two, separate nucleic acids encoding the TRA and TRB of a TCR construct.

The term "capable of specifically binding" or "recognizing" or "specific for" a given antigen, as used herein, means that the TCR construct can specifically bind to and immunologically recognize said epitope, preferably with high affinity. Affinity can be analyzed by methods well known to the skilled person, e.g. by BiaCore.

One of the advantages of the present invention is that it is not required that immunogenic epitopes from the antigen presented on a specific MHC allele are known. With the method of the invention, it is possible to analyze T cell responses to antigens, where epitopes are naturally processed and presentation may occur via each possible MHC. Thus, the method of the invention may be used to identify a TCR specific for a defined antigen without prior knowledge of the epitope. The defined antigen may even be one of a plurality of antigens, e.g., a plurality of antigens of a specific virus, or all antigens of a specific virus, if both the antigen presenting cells in step a and the library in step b present epitopes of said antigens.

A further advantage is that the method of the invention renders it possible to identify TCRs specific for immunodominant peptide epitopes, and to provide said peptide epitopes. It has been observed that certain peptide-MHC (pMHC) combinations induce a dominant T cell response over other pMHC combinations derived from the same antigen even though both combinations are predicted to have high binding affinities. Additionally, this method may also enable the isolation of TCRs targeting subdominant epitopes, if the number of PBMCs screened is largely increased.

As therapy of humans is of most interest, it is preferred that the method is carried out in the human system, i.e., the donor is human, and, accordingly, human MHC I or MHC II, in particular, MHC I molecules, and APCs are used. It is of course also possible to use T cells from a murine donor, which are restricted to human MHC molecules (14,15) or murine T cells expressing human T cell receptors (16). Alternatively, other, e.g., completely murine, rat, goat, rabbit, guinea pig systems may be used if provision of a TCR from that species is desired.

Preferably, the T cells stimulated in step a are in the form of PBMCs, i.e., not separated from other mononuclear cells. This may be beneficial because it provides a more natural environment and excludes the need for additional purification steps. TILs isolated from a donor may also be used. Alternatively, purified T cells, or purified $CD4^+$ or, preferably, $CD8^+$ T cells may be used.

The professional APCs are preferably autologous APCs, i.e., they are isolated from the same donor as the PBMCs. They can however also be heterologous APCs, as long as they share at least one MHC allele, preferably, all MHC I or II (preferably MHC I) alleles with the donor. Most preferably, the professional APCs are dendritic cells, in particular, mature dendritic cells. The professional APCs present epitopes of the defined antigen on the MHC after endogenous processing of the antigen. The antigen is preferably provided to the inside of the professional APCs as RNA, DNA, protein or polypeptide to enable endogenous processing and presentation by the APCs. Therefore, prior knowledge of the epitope is not required. For example, stable or transient expression after transfection is possible.

The stimulation of T cells in step a is carried out for 7-42 days, most preferably for 14-28 days. The ratio of PBMCs to professional APCs preferably is about 5:1 to 20:1, most preferably, about 10:1. T cells are stimulated in medium containing cytokines favoring T cell proliferation; preferably low concentrations of IL-2 (e.g., 15-25 U/ml, preferably, about 20 U/ml), IL-7 (e.g., 2.5-7.5 U/ml, preferably, about 5 U/ml) or IL-15 to prevent antigen-unspecific T cell proliferation in the specific culture settings. Proliferating PBMCs may be split at ratios of about 1:2 to 3:4. A second stimulation with professional APC presenting an epitope of the antigen after endogenous processing is possible.

The cells enriched for antigen-specific T cells in step a are further contacted with a library of cells in step b, wherein each cell expresses a single MHC allele, wherein the library comprises cells expressing all MHC I or II alleles present in the donor, and wherein the cells of said library present epitopes of said defined antigen.

It is preferred throughout the invention that the MHC is MHC I. The T cells stimulated by these cells, which express MHC I, will be CD8$^+$ T cells, and, typically, epitopes from intracellular proteins will be presented.

In a preferred embodiment, the library consists of K562 cells stably expressing one MHC I allele each. Exemplary K562 libraries are described below or disclosed by Zeng et al. (19). Cells of the library may be of other origin than K562 cells, comprising any human or non-human APCs, e.g., lymphoblastoid cell lines (LCL) or NIH/3T3 cells.

The MHC cell library used herein was generated by stable transduction of the human K562 cell line (20,21) with single human MHC I alleles (HLA-A, -B and -C). K562 cells are of human erythroleukemic origin and lack expression of endogenous MHC I and MHC II alleles (22). However, they express β-2 microglobulin, and upon transgenic expression of an MHC I a chain they possess a fully functional antigen-processing and presentation machinery (19,23,24). K562 cells express ICAM-1 and LFA-3, which are needed to form an effective immune synapse (24). Furthermore, it was possible to genetically modify these cells e.g. via retroviral transduction to stably express single MHC I alleles and to introduce antigenic sequences e.g. via transfection with in vitro transcribed (ivt) RNA.

In one embodiment, the present invention thus also provides a K562-based MHC cell library, cells of which may be employed in the method of the invention. Said library comprises K562 cells, each cell expressing one of the following MHC I alleles:

| K562-based MHC cell library | | |
|---|---|---|
| HLA-A* | HLA-B* | HLA-C* |
| 01:01 | 07:02 | 01:02 |
| 02:01 | 07:04 | 02:02 |
| 03:01 | 08:01 | 03:03 |
| 03:05 | 15:01 | 03:04 |
| 11:01 | 18:01 | 04:01 |
| 23:01 | 27:05 | 05:01 |
| 24:02 | 35:01 | 06:02 |
| 26:01 | 35:08 | 07:01 |

| K562-based MHC cell library | | |
|---|---|---|
| HLA-A* | HLA-B* | HLA-C* |
| 29:02 | 38:01 | 07:02 |
| 31:01 | 40:01 | 12:03 |
| 33:01 | 41:02 | 15:02 |
| 66:01 | 44:02 | 16:01 |
| 68:02 | 44:03 | 16:02 |
| 68:24 | 47:01 | 17:01 |
|  | 49:01 |  |
|  | 51:01 |  |
|  | 56:01 |  |
|  | 57:01 |  |
|  | 57:03 |  |
|  | 58:01 |  |

Using K562 cells as artificial APCs scaffold has several advantages. Compared to LCLs, K562 cells lack viral sequences from herpes viruses like EBV (25,26). This is an important feature of the K562-based APC system to avoid EBV-specific T cell activation during analysis of bulk T cell samples, which may naturally contain EBV-specific T cells. Compared to acellular artificial APCs, in a cellular APC system pMHC presentation occurs at physiological levels at the cell surface of an intact cell membrane, which resembles the most native environment for TCR binding. Dominant expression of one MHC minimizes allo-recognition of TCRs. The capability of MHC-transduced K562 to present pMHC at the cell surface shows that antigen processing and MHC expression in parental K562 is not a general defect, but due to silencing of the endogenous MHC locus. K562 cells express a constitutive proteasome compared to immune proteasome-expressing DCs, which resembles antigen processing by a typical tumor cell (27). TCR-transduced T cells cocultured with K562 cells in the absence of the target antigen showed no background IFNγ release and CD137 up-regulation minimizing unspecific activation of T cells.

The attributes of K562 cells discussed above made them the preferred cellular artificial APC system to establish an MHC cell library as a target for the analysis of TCRs without prior knowledge of epitope specificity and MHC restriction. In principle, any target antigen may be expressed in K562 cells, which includes pathogen-derived antigens as well as tumor-associated antigens (TAA), cancer testis antigens (CTA) and lineage antigens. For cancer immunotherapy, tumor-specific antigens (TSA) are of particular interest to identify TCRs specific for viral epitopes or mutation-derived epitopes.

Latouche and Sadelain used plate adherent mouse fibroblast NIH/3T3 cells, which stably expressed single human MHC alleles (28) and thereby achieved endogenous presentation of epitopes in the context of human MHC complexes. NIH/3T3 cells have been successfully used to expand CMV-specific T cell lines for use in post-transplant adoptive T cell therapy (29), and may be used as an alternative library in the context of the invention.

Alternatively, the MHC may be MHC II. In that case, the library of cells preferably comprises MHC II expressing cells, such as K562 cells transfected with one MHC II allele each. An exemplary library is disclosed by Butler et al. (30). Alternatively, single MHC II-expressing cell libraries may be used which are based on human RM3 (Raji) B cells, which were generated following random mutagenesis with ethane methylsulfonate (EMS) to knock out the MHC II locus (31). The T cells stimulated by these cells will be CD4$^+$, and, typically, epitopes from secreted proteins, proteins of different cell compartments, membrane proteins or cross-presented proteins will be presented.

The cells of the library, in particular K562 cells, may further express costimulatory molecules, e.g., CD40, CD40L, CD70, CD80, CD83, CD86, ICOSL, GITRL, CD137L and/or CD252, so that the cells can be tailored for the optimal contacting of T cell subsets. Sets of costimulatory molecules may be CD80, CD86 and CD137L, or CD80, CD83, CD64 (30), or CD80, CD70 and CD137L (19). This may amplify the T cell response to clearly detect antigen-specific IFNγ release and CD137 expression and may lead to the detection of a wider range of TCRs with regard to affinity. However, to isolate high affinity TCRs, it may be preferably if the cells of the library, in particular the K562 cells, do not express any further costimulatory molecules. Furthermore, cells of the library, in particular K562 cells, may express molecules, which enhance antigen processing and presentation, e.g. HLA-DM and CD74.

The cells of the library present epitopes of the defined antigen on their MHC molecules after endogenous processing. Preferably, they stably express the complete full-length antigen, e.g., after transfection with antigen-encoding ivtRNA. Transient expression may also be used. Accordingly, prior knowledge of the epitope is not required.

Contacting of the library with T cells is performed between 12 and 36 hours, preferably, 18-22 hours or about 20 hours to achieve optimal activation of antigen-specific T cells within the T cell sample. Preferably, the addition of cytokines is avoided during contacting to prevent T cells from unspecific activation.

Those T cells carrying a TCR specific for an epitope presented by the cells of the library are activated. Accordingly, they can be selected based on an activation marker (step c), so that prior knowledge of the T cell epitope and MHC restriction element is not required. T cells up-regulate activation markers upon engagement of the TCR with the cognate pMHC complex on target cells. TCR signaling together with costimulatory signals induces short-term expression of activation molecules like CD25, CD69, CD107, CD137 and/or CD154, which can be used as markers for detecting and isolating antigen-specific T cells (32), e.g., by FACS or MACS. CD137 was shown to be a specific marker for the isolation of antigen-specific $CD8^+$ T cells (33,34). Sorting based on CD137 expression, e.g., by FACS, is a preferred method for selection of specific T cells. In one embodiment, this is combined with measurement of IFNγ release e.g. by enzyme-linked immunosorbant assay (ELISA) or by cytokine capture of IFNγ by FACS. Measuring IFNγ release e.g. by ELISA is a standard method to evaluate functional activity of T cell samples.

Cytokine capture assays provide an alternative tool to detect and isolate functionally active T cells without prior knowledge of pMHC specificity (35,36). $CD8^+$ T cells activated through cognate pMHC I release vesicles with cytokines like IFNγ and TNFα. Detection and isolation of individual T cells upon cytokine secretion has been facilitated through the development of cytokine capture assays in combination with FACS or MACS analysis (36,37). Cytokine capture assays provide an attractive alternative to T cell activation markers for the sorting of T cells, which were activated by TCR signaling.

After selection of activated T cells, the nucleic acids encoding the TCR alpha and TCR beta chain of the T cell receptor of said T cells are directly isolated. E.g., RNA may be isolated to generate cDNA via 5' rapid amplification of cDNA ends (RACE) of TCR alpha and TCR beta genes followed by PCR amplification. PCR products may be cloned into expression plasmid to transform bacteria. Each bacterial colony may be regarded as containing one sequencing vector with one PCR TCR alpha or TCR beta gene fragment. Vector DNA of numerous bacterial colonies may be prepared, followed by sequencing of vector inserts (TCR alpha or TCR beta gene fragments). Sequencing results of each bacterial colony may be analyzed, e.g., by using IMGT/V-Quest. Frequencies of identical TCR alpha or TCR beta chains reflect the proportion of identical T cell clonotypes within the sorted T cell sample. Another strategy to analyze TCR alpha and TCR beta gene sequences of sorted T cells is the use of next-generation sequencing approaches. For example, PCR products of TCR alpha and TCR beta genes, which were ligated into sequencing vectors may be transformed into bacteria and grown in flasks containing selective medium and followed by preparation of the vector DNA. Vector DNA preparations may be directly used for next-generation sequencing analysis. Frequency of vectors containing identical TCR alpha or TCR beta genes are regarded to be representative for the initial amount of T cells of the same clonotype within the sample of sorted T cells. Frequency matching of TCR alpha and TCR beta chains within a T cell sample can be used for analyzing pairing for functional TCRs (38), e.g., TCRs which had accounted for antigen-MHC-specific IFNγ release and CD137 upregulation. Sensitivity of these methods enables detailed analysis of TCR repertoires within T cell samples. Matching the frequencies of TCR alpha and TCR beta chains additionally enables the reconstitution of abundant TCR chain pairs from T cell samples, thus making resource-intensive T cell clone culture dispensable. Long-term cultivation is necessary to expand T cell clones in culture, which may only favor the outgrowth of T cells, which had a naïve or central memory phenotype, therefore excluding T cells from the analysis, which have limited growing capacity in vitro. For the analysis of TCR repertoires it is thus an advantage to screen and sort antigen-MHC-specific T cell responses after only 14 to 28 days of antigen-specific enrichment.

Thus, preferably, if after analysis of the nucleic acids encoding the TCR alpha and TCR beta chains of the selected population of T cells, more than one TCR alpha and TCR beta chain is identified, the frequency of the TCR alpha and TCR beta chains in the population is analyzed and TCR alpha and TCR beta chains constituting a TCR capable of recognizing the epitope are matched based on their frequency.

Alternatively, further analysis may be carried out, e.g., generation of T cells carrying combinations of different predominant TCR alpha and TCR beta chains, and analysis of their activation by cells of the library used in step b.

The TCR alpha and beta chains may be modified, leading to TCR alpha chain constructs (TRA) and TCR beta chain constructs (TRB) of the invention. Optionally, codon usage of the TRA and TRB may be optimized to enhance expression of the TCR in recombinant T cells. Furthermore, human variable regions may be combined with murine constant regions (39), or a minimal murine constant region, i.e., human constant regions containing only defined amino acids from the murine constant region (40) and additionally comprising an additional cysteine bridge (41,42), which increases preferential binding of transgenic TCR chains to each other and reduces pairing with endogenous TCR chains expressed by recipient T cells.

Further optimization of expression is possible, e.g., by generating single-chain TCR constructs harboring the variable regions of the TRA and TRB to avoid pairing of endogenous TCR chains with introduced chains and to enhance functional activity. Furthermore, soluble receptor molecules and fusion proteins may be generated containing the variable regions of the TRA and TRB chain genes and e.g. antibody domains.

T cells specific for an epitope from a defined antigen presented on an MHC may be generated by expressing the nucleic acids encoding the TRA and TRB. If such T cells are intended for therapy of a patient, it is preferred to use autologous T cells. Alternatively, an allogeneic setting is possible, using immune suppression.

Analysis of activation of T cells transfected with suitable TCR constructs with cells of the library expressing specific MHC alleles may easily be used to analyze MHC restriction of the TCR.

The present invention further provides a method for identifying an epitope of a defined antigen capable of being presented by an MHC, comprising carrying out steps a-d of the method of the invention described above, and identifying the epitope capable of activating said selected T cells, or T cells modified with nucleic acids encoding the TRA and TRB constituting the TCR construct. Epitope mapping strategies are known in the art. For example, cells of the library expressing the relevant MHC allele may be transfected with minigenes covering sections of the relevant antigen, and responses, e.g., IFNγ secretion, analyzed to find the section harboring the epitope. Peptide pulsing with external peptides may also be helpful. Epitope prediction may be employed as part of such a strategy, but it is important to note that, as shown by the experiments described below that TCR specificity not necessarily matches predicted data from epitope prediction algorithms.

Furthermore, the epitope identified to induce antigen-specific T cell responses, which is demonstrated by the isolation of antigen-specific TCRs accounting for this response, may be used to develop vaccine formulations containing the epitope sequence. The method described in the inventions ensures the recognition of epitopes on MHC, which are endogenously processed and presented by cells expressing a defined antigen. Application of the epitope-containing vaccine may provide T cell immunity to patients to clear cells, which naturally express the defined antigen.

In summary, the method of the invention has several advantages over conventional methods of providing TCR constructs which may be used, e.g., for adoptive T cell therapy. For example, the full repertoire of T cells is covered, e.g. including all cognate MHC I restriction elements of a given donor. The method also allows for detection of T cells with desired antigen specificity, but does not require previous knowledge of epitopes. It is based on the recognition of endogenously processed and presented epitopes without predetermination of selected epitopes. Different epitopes from one antigen have an expression hierarchy defined as immune dominance TCR constructs identified by the method of the invention recognize the immune dominant epitopes within target antigens, which are presented most efficiently on one of the six MHC I alleles. The method also allows for the identification of T cells recognizing subdominant epitopes from the same antigen. Finally, the method allows for parallel detection of different T cell clonotypes recognizing the same antigen.

The invention also provides novel TCR constructs and the epitopes recognized by these TCR constructs, which are obtainable by the method of the invention and/or disclosed below, as well as nucleic acids, e.g., vectors, such as expression vectors, encoding these TCR constructs or the respective TRA and TRB or fragments thereof, such as variable fragments or the CDR3 region of the TRA or TRB, or transgenic T cells expressing said nucleic acids.

Human papillomavirus (HPV) infection is the primary cause for the development of cervical cancers, anogenital cancers and head and neck squamous cell carcinomas (43, 44). Oncogenic HPV types accounting for approximately 610 000 cancer cases per year worldwide.

The most prevalent oncogenic type is HPV16 accounting for over 50% of cervical cancer cases. HPV16 E6 and E7 have transforming potential and are regarded as driving oncogenes (45,46). HPV16 E5 has been shown to have oncogenic potential, because of its ability to transform fibroblasts in vitro (47,48). Furthermore, it was found that E5 is expressed in biopsies of invasive cervical cancer indicating an important role of E5 in initiating and maintaining the transformed phenotype of malignant keratinocytes (49-51).

While prophylactic vaccination programs together with medical screenings and interventions will reduce HPV-related morbidity in several countries over the next centuries, HPV will remain a significant global health issue with a need for therapeutic treatments of cervical cancer and other HPV-caused cancers.

Attempts of therapeutic treatment of HPV-associated malignancies have been reported in numerous studies. However, only one phase I/II study applying synthetic long peptides covering the complete HPV16 E6 and E7 sequence has shown data of patients, which experienced regression of high-grade vulvar intraepithelial neoplasias (VIN) in more than 50% of the patients. This response was associated with HPV-specific T cell responses (52). Nevertheless, comparable results targeting CIN lesions and cervical cancer are lacking, suggesting that current attempts of therapeutic vaccination targeting HPV16 E6 and E7 do not overcome immune escape mechanisms of HPV (52,53). Furthermore, potent TCRs targeting E6 and E7 are lacking, which allow validation of immunotherapeutic treatment of HPV-induced malignancies.

As further therapeutic strategies are sought to treat HPV-induced cancers, the inventors' efforts concentrated on isolation of antigen-specific TCRs for HPV-derived antigens and the identification of immunogenic epitopes from these antigens using the method described above. HPV16 E5, E6, E7 and L1 were used as antigens.

Cytomegalovirus (CMV), also designated human herpes virus 5 (HHV-5), is a member of the herpes virus family. CMV infections resemble other herpes virus infections as they are controlled by $CD8^+$ and $CD4^+$ T cells, which occur at very high precursor frequency in CMV-seropositive individuals (54). CMV infection is usually asymptomatic in immune competent individuals and persists lifelong in a latent stage in up to 90% of the population. CMV disease may manifest in some immune compromised individuals after birth or after hematopoietic stem cell transplantation or solid organ transplantation causing a total of 5,600 severe disease cases with 560 deaths per year in the USA (54). CMV has widely been regarded as non-oncogenic, as infection does not seem to lead to cell transformation, but may opportunistically infect malignant cells. Recent studies have associated CMV with glioblastoma, questioning that CMV is a non-oncogenic virus (55-58). In light of this, the inventors have decided to also investigate TCRs specific for CMV antigens.

A strong T cell response to HPV16 E5 in combination with HLA-B*15:01 was observed upon screening with antigen-expressing K562 cells of the MHC cell library. Additionally, a CMV pp65-specific T cell response was observed over HLA-B*07:02. T cell samples responding to one antigen-MHC combination were directly sorted and analyzed for TCR gene sequences. Predominant TCR genes in a sample were cloned into a retroviral expression vector and testing was assessed by transducing different TCR alpha and beta chain combinations into PBMCs. A functional HPV16 E5-specific TCR and a functional CMV pp65-specific TCR could be reconstituted, which recognized endogenously processed epitopes presented on HLA-B*15:01 and B*07:02, respectively.

In particular, the invention thus provides an HPV E5-specific TCR construct, which may be used, e.g., for TCR gene therapy to treat HPV infection, in particular, HPV-induced malignancies. The invention provides a nucleic acid encoding a TRA and/or TRB of a TCR construct specific for an epitope of human papillomavirus 16 oncoprotein E5 in complex with a human MHC I. The nucleic acid may be obtainable or obtained from the method of the invention described herein.

The inventors provide a TCR construct specific for an epitope of human papillomavirus 16 oncoprotein E5 in complex with HLA-B*15:01, which preferably comprises SEQ ID NO: 1. The TCR construct preferably also recognizes an N-terminally longer version of the epitope, e.g., it may consist of SEQ ID NO: 1, 45, 47, 49, 51, 52 and 57. The inventors showed for the first time that these peptides are endogenously processed and may be presented on HLA-B*15:01, and may thus be the target of TCR recognition. Besides TCR gene therapy, vaccines comprising peptides of SEQ ID NO: 1, 45, 47, 49, 51, 52 and 57 may be a second strategy to provide T cell immunity in HLA-B*15:01-positive patients. Around 12% of the German population carry at least one HLA-B*15:01 allele. Population studies in China, South Korea and Japan have been found to have even higher B*15:01 allele frequencies (59).

Specificity of a TCR or TCR construct is mainly defined by the CDR3 regions of the TCR. The TCR construct of the invention specific for the E5 epitope presented on HLA-B*15:01 comprises a TRA comprising a CDR3 of SEQ ID NO: 2 or a CDR3 having at least 84%, preferably, at least 92% sequence identity thereto, i.e. there may be one or two substitutions, insertions or deletions. If there are mutations, conservative substitutions are preferred. SEQ ID NO: 2 is a preferred sequence of a CDR3 of a TRA of the invention. In one embodiment, the TRA comprises the CDR3 of SEQ ID NO: 2, CDR1 of SEQ ID NO: 64 and CDR2 of SEQ ID NO: 65.

The variable region of the TRA preferably comprises SEQ ID NO: 3 or has a sequence identity of at least 80%, preferably, at least 90% or at least 95% to SEQ ID NO: 3, wherein, preferably, the variable region comprises SEQ ID NO: 2. The variable region may be encoded by a nucleic acid of SEQ ID NO: 60. The TRA preferably has a sequence identity of at least 80%, preferably, at least 90%, at least 95% or 100% to SEQ ID NO: 4 or consists thereof, wherein the constant region preferably is a murine constant region or a minimal murine constant region to enhance pairing of transgenic TCR chains. Alternatively, the constant region may also be human, which minimizes the risk for immune recognition by immune cells of the recipient.

A preferred, codon-optimized nucleic acid encoding the TRA of the TCR construct specific for the HPV E5 epitope of the invention is SEQ ID NO: 5.

The TCR construct of the invention specific for the E5 epitope presented on HLA-B*15:01 comprises a TRB comprising a CDR3 of SEQ ID NO: 6 or a CDR3 having at least having at least 84%, preferably, 92% sequence identity thereto, i.e. there may be one or two substitutions, insertions or deletions. Conservative substitutions are preferred. SEQ ID NO: 6 is a preferred sequence of a CDR3 of a TRB of the invention. In one embodiment, the TRB comprises the CDR3 of SEQ ID NO: 6, CDR1 of SEQ ID NO: 66 and CDR2 of SEQ ID NO: 67.

The variable region of the TRB preferably comprises SEQ ID NO: 7 or has a sequence identity of at least 80%, preferably, at least 90% or at least 95% to SEQ ID NO: 7, wherein, preferably, the variable region comprises SEQ ID NO: 6. The variable region may be encoded by a nucleic acid of SEQ ID NO: 61. The TRB preferably has a sequence identity of at least 80%, preferably, at least 90%, at least 95% or 100% to SEQ ID NO: 8 or consists thereof, wherein the constant region preferably is a murine constant region or a minimal murine constant region to enhance pairing of transgenic TCR chains. Alternatively, the constant region may also be human, which minimizes the risk for immune recognition. A preferred, codon-optimized nucleic acid encoding the TRB is SEQ ID NO: 9.

The invention also provides a nucleic acid encoding both TRA and TRB specific for the HPV E5 epitope in a suitable expression cassette, e.g., for TCR gene therapy to treat HPV infections, in particular, HPV-induced malignancies, e.g., comprising the sequence according to SEQ ID NO: 40.

Based on the sequences provided by the method of the invention, it is possible to carry out affinity maturation of the TCR sequences (60,61). Non-synonymous nucleotide substitutions which lead to amino acid exchanges in the CDR3 sequence may lead to enhanced affinity of the TCR to target antigen. Furthermore, TCR sequence changes in other parts of the variable TRA and TRB regions may change, preferably increase, affinity of the TCR construct to the pMHC complex. It is preferred that TCR constructs varying from the specific sequences provided retain exclusive specificity for the target antigen provided. Accordingly, it is preferred that adoptive transfer of T cells expressing the TCR construct of the invention has no significant negative effects on healthy tissue.

The invention further provides a CMV pp65-specific TCR construct, which may be used, e.g., for TCR gene therapy to treat CMV infection or CMV-induced malignancies. The invention provides a nucleic acid encoding a TRA and/or TRB of a TCR construct specific for an epitope of human CMV protein pp65 in complex with a human MHC I. The nucleic acid may be obtainable or obtained from the method of the invention described herein.

The inventors provide a TCR construct specific for an epitope of human CMV protein pp65 in complex with HLA-B*07:02, which preferably comprises SEQ ID NO: 10 or consists thereof. The CMV pp65-specific TCR is restricted to HLA-B*07:02. HLA-B*07:02 is one the most frequent HLA-B alleles and found in about 23% of the German population (59). Epitope recognition by T cells may be the basis for the development of CMV vaccines inducing T cell immunity in HLA-B*07:02-positive patients.

The TCR construct of the invention specific for this epitope/MHC complex comprises a TRA comprising a CDR3 of SEQ ID NO: 11, which accordingly is a preferred CDR3 of a TRA of the invention. In one embodiment, the TRA comprises the CDR3 of SEQ ID NO: 11, CDR1 of SEQ ID NO: 68 and CDR2 of SEQ ID NO: 69. The variable region of the TRA preferably comprises SEQ ID NO: 12 or has a sequence identity of at least 80%, preferably, at least 90% or at least 95% to SEQ ID NO: 12, wherein the variable region comprises SEQ ID NO: 11. The variable region of the TRA may be encoded by a nucleic acid according to SEQ ID NO: 62. The TRA preferably comprises SEQ ID NO: 13 or consists thereof, wherein the constant region is a murine constant region or a minimal murine constant region to enhance pairing of transgenic TCR chains. Alternatively, the constant region may also be human, which minimizes the risk for immune recognition. A preferred, codon-optimized nucleic acid encoding the TRA chain of the TCR specific for the CMV pp65 epitope of the invention is SEQ ID NO: 14.

The TCR construct of the invention specific for this epitope/MHC complex comprises a TRB comprising a CDR3 of SEQ ID NO: 15, which accordingly is a preferred CDR3 of a TRB of the invention. In one embodiment, the TRB comprises the CDR3 of SEQ ID NO: 15, CDR1 of SEQ ID NO: 70 and CDR2 of SEQ ID NO: 71. The variable region of the TRB preferably comprises SEQ ID NO: 16 or has a sequence identity of at least 80%, preferably, at least 90% or at least 95% to SEQ ID NO: 16, wherein, the variable region comprises SEQ ID NO: 15. The variable region of the TRA may be encoded by a nucleic acid according to SEQ ID NO: 63. The TRB preferably comprises SEQ ID NO: 17 or consists thereof, wherein the constant region is a murine constant region or a minimal murine constant region to enhance pairing of transgenic TCR chains. Alternatively, the constant region may also be human, which minimizes the risk for immune recognition. A preferred, codon-optimized nucleic acid encoding the TRB chain is SEQ ID NO: 18.

The invention also provides a nucleic acid encoding both TRA and TRB specific for the CMV pp65 epitope in a suitable expression cassette, e.g., for TCR gene therapy to treat CMV infections, in particular CMV disease and CMV-induced malignancies, e.g., comprising the sequence according to SEQ ID NO: 41.

The nucleic acids of the invention may be provided as vectors comprising the nucleic acids of the invention encoding the TRA and/or TRB of the invention, e.g., vectors in which the TRA and/or TRB are operably linked to a promoter suitable for expression in T cells, such as human T cells. Preferably, said promoter is a heterologous promoter, i.e., it is not linked to TCR alpha or beta genes in naturally occurring cells, in particular, in human T cells. The promoter may be a constitutive or inducible promoter, preferably a myeloproliferative sacrcoma virus (MPSV), a CMV, a CAG or an EF1α promoter. The nucleic acids of the invention may be provided as RNA, as retroviral vectors, as γ-retroviral vectors, as lentiviral vectors or as transposon-based vectors. In one embodiment, the vector is suitable for TCR gene therapy of a human patient. Preferably, the vector is MP71. Nucleic acids of the invention, e.g., encoding TRA and TRB may be fused via a genetic linker, preferably a virus-derived 2A element, to provide a single transgene cassette encoding both chains of a functional TCR construct.

The invention also provides proteins encoded by the nucleic acids of the invention, or fusion proteins thereof, in particular TRA and/or TRB encoded by the nucleic acids of the invention and specific for the disclosed antigens, e.g., for the epitope of HPV16 oncoprotein E5. A TRA and/or TRB of the invention may comprise all characteristics or domains corresponding to its native counterpart, but this is not essential. Preferably, the TRA and TRB comprise at least a variable region, or a variable and a constant region, e.g., the variable and/or constant region having at least 80%, at least 90% or at least 95% sequence identity to a human variable or constant region. For adoptive T cell therapy, it is preferred that the TCR construct is a TCR comprising full length TCR alpha and beta chains comprising variable, constant and transmembrane regions.

The construct may also be a fusion protein, for example, variable regions of the TCR chains may be fused to Ig domains, e.g., an IgG constant domain, preferably, anti-CD3 antibody domains in a fusion protein of the invention, e.g., to provide soluble monoclonal TCR reagents to target malignant cells expressing the respective pMHC at the cell surface and engaging T cells via e.g. an anti-CD3 targeting domain to provide effector functions to the target cells (63).

Single chain constructs (scTCR) are encompassed as well as heterodimeric TCR constructs. A scTCR can comprise a variable region of a first TCR chain construct (e.g., an alpha chain) and an entire (full-length) second TCR chain (e.g., a beta chain), or vice versa. Furthermore, the scTCR can optionally comprise one or more linkers which join the two or more polypeptides together. The linker can be, for instance, a peptide which joins together two single chains, as described herein. Also provided is such a scTCR of the invention, which is fused to a cytokine, e.g., a human cytokine, such as IL-2, IL-7 or IL-15.

The TCR construct according to the invention can also be provided in the form of a multimeric complex, comprising at least two scTCR molecules, wherein said scTCR molecules are each fused to at least one biotin moiety, and wherein said scTCRs are interconnected by biotin-strepavidin interaction to allow the formation of said multimeric complex. Also provided are multimeric complexes of a higher order, comprising more than two, e.g., four, scTCR of the invention.

The TCR construct of the invention can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and particles (e.g., gold particles or magnetic particles).

The invention also relates to a host cell, preferably, a CD8$^+$ T cell comprising a nucleic acid encoding the TRA and TRB of a TCR construct of the invention, in particular a TCR construct specific for an epitope of human cytomegalovirus protein pp65, or, preferably, for an epitope of human papillomavirus 16 oncoprotein E5, and expressing said TCR construct. The TRA and TRB are preferably expressed from a heterologous promotor, e.g., as described above. The T cell preferably is a human T cell. It may be isolated from a patient infected with the relevant virus, in particular, a patient suffering from a malignancy associated with said virus, such as cervical cancer, anogenital cancer and head and neck cancer in the case of HPV. The patient expresses the MHC to which the epitope recognized by the TCR is restricted. The T cell may be a central memory T cell or a naïve T cell.

The invention also relates to such a host cell, e.g., T cell, or a nucleic acid of the invention for use in medicine, e.g., in a pharmaceutical composition. Such a pharmaceutical composition may be used for treatment of a patient infected with a) human papillomavirus 16, wherein the TCR is specific for an epitope of human papillomavirus 16 oncoprotein E5 and wherein the patient is HLA-B*15:01-positive; or b) human cytomegalovirus, wherein the TCR is specific for an epitope of human cytomegalovirus protein pp65 and wherein the patient is HLA-B*07:02-positive.

For use in medicine, the TCR construct comprising both TRA and TRB is employed, either in nucleic acid, protein or T cell form. It may be helpful to screen HPV-infected patients for expression of the E5 antigen prior to therapy, and treat only those patients with E5 expression.

The pharmaceutical composition may also be for use in prevention of infection or in reducing infection with a pathogen such as a virus, e.g., a) human papillomavirus 16, wherein the TCR is specific for an epitope of human papillomavirus 16 oncoprotein E5 and wherein the patient is HLA-B*15:01-positive; or b) human cytomegalovirus, wherein the TCR is specific for an epitope of human cytomegalovirus protein pp65 and wherein the patient is HLA-B*07:02-positive.

For example, pharmaceutical compositions wherein the TCR is specific for an epitope of human papillomavirus 16 oncoprotein E5 and wherein the patient is HLA-B*15:01-positive may be used for prevention of cervical cancer in a patient infected with HPV16, e.g., if premalignant high-grade lesions of the cervix are detected. Pharmaceutical compositions wherein the TCR is specific for an epitope of human cytomegalovirus protein pp65 and wherein the patient is HLA-B*07:02-positive may be used for treatment of a patient after transfer of hematopoietic stem cells to prevent CMV disease or reduce symptoms thereof in said patient.

The invention also teaches a method of treatment of a patient in need thereof (e.g., infected with a virus such as HPV16 or CMV, or suffering from a malignancy associated with said virus), or of reducing infection with a virus, or symptoms of said infection, comprising administering to said patient a suitable recombinant T cell, or a nucleic acid of the invention. Treatment or prevention of post transplantation CMV disease (64,65) is also possible with T cells expressing or nucleic acids encoding the TCR of the invention specific for the CMV pp65 epitope.

The invention also relates to a nucleic acid encoding a fragment of human papillomavirus 16 oncoprotein E5 having a length of up to 40 amino acids comprising an epitope, or a peptide fragment of human papillomavirus 16 oncoprotein E5 having a length of up to 40 amino acids comprising an epitope, wherein the epitope is capable of being recognized by the TCR construct of the T cell of the invention. Such E5 fragments may be advantageously used in vaccination, e.g., for synthetic long peptide vaccination. Preferably, the nucleic acid encodes an epitope, or the peptide consists of an epitope, which can be identified by the method of the invention for identification of an epitope. Preferably, the epitope is an epitope of human papillomavirus 16 oncoprotein E5 capable of being recognized by the TCR construct described above. The E5 epitope, which has been identified for the first time by the method of the invention, preferably comprises SEQ ID NO: 1 and is selected from the group consisting of SEQ ID NO: 1, 45, 47, 49, 51, 52 and 57.

The invention also relates to said nucleic acid encoding said E5 peptide fragment or said epitope, or to said peptide fragment or epitope for use in medicine, preferably, for preventing infection (or reducing infection) with human papillomavirus 16, for prevention of cervical cancer in a patient infected with HPV16, e.g., if premalignant high-grade lesions of the cervix are detected, or for treatment of HPV16 infection, in particular, a HPV16-induced malignancy. Vaccines providing said epitope may be for administration to subjects, e.g., patients, who are HLA-B*15:01-positive.

The invention is further illustrated by the examples below, which are intended to exemplify the invention, and not to limit its scope. All references cited herein are herewith fully incorporated. All embodiments of the invention disclosed herein can be combined.

FIGURE LEGENDS

FIG. 1 Retroviral HLA vectors. Scheme of the γ-retroviral vector MP71 carrying different HLA alleles fused to an (a) IRES-GFP or (b) IRES-CFP expression marker.

Figure 2:
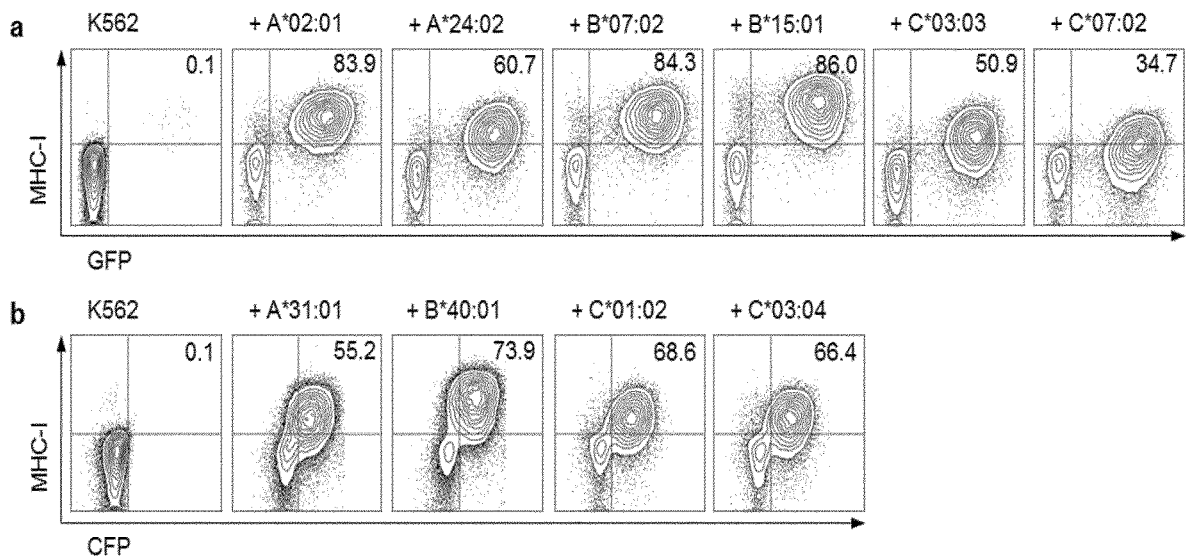

FIG. 2 MHC class I cell library. K562 cells were transduced with the retroviral vector MP71 carrying an (a) MHC-IRES-GFP or an (b) MHC-IRES-CFP cassette. Shown is a selection of FACS plots of 10 MHC transductions covering all MHC class I alleles of two T cell donors. GFP and CFP expression indicate transduction rates. MHC surface expression of GFP- or CFP-positive cells is shown by MHC class I antibody staining and indicated in percentages.

Figure 3:
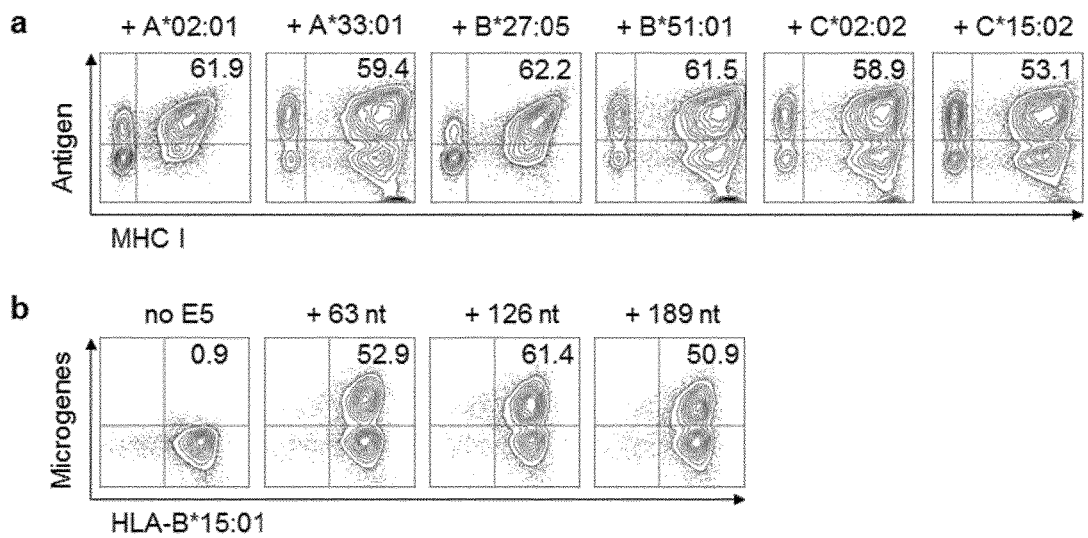

FIG. 3 Examples of stable antigen expression in the MHC cell library. K562 cells were stably transduced with antigen (HPV16 E7) fused to an IRES-mCherry marker and detected by flow cytometry measuring of mCherry expression. MHC I alleles are fused to IRES-GFP marker and expression is indicated by flow cytometric detection of GFP. Percentages of MHC-IRES-GFP/antigen-IRES-mCherry double positive cells are depicted in the FACS plots. (a) K562 cells of the MHC cell library were stably transduced with E7. (b) MHC (HLA-B*15:01)-transduced K562 cells were stably transduced with the truncated microgene constructs of E5, which were used for epitope mapping (nt, nucleotides).

Figure 4:
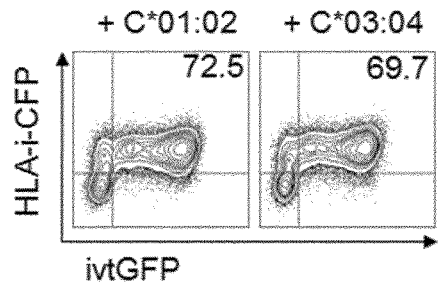

FIG. 4 Expression of antigens from ivtRNA in target cells. Single MHC-transduced K562 cells expressing IRES-CFP marker were transfected via electroporation with ivtRNA encoding GFP. Expression of GFP was measured 5 h after electroporation and served as control for transfection efficiency.

Figure 5:
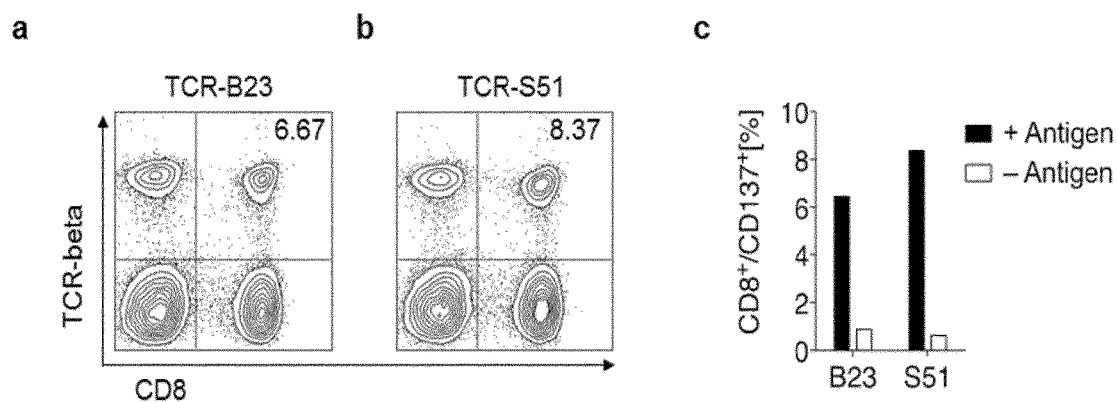

FIG. 5 Induction of antigen-specific T cell response upon coculture with K562 cells of the MHC cell library. (a) TCR-B23 and (b) TCR-S51 were stably transduced into T cells, which were stained for CD8 and transgenic TRB expression and analyzed by flow cytometry. (c) TCR-transduced T cells were cocultured with K562-B*27:05 target cells 3 h after E7co ivtRNA transfection. CD137 expression was measured by flow cytometry. H$_2$O-transfected K562-B*27:05 target cells served as a negative control.

Figure 6:
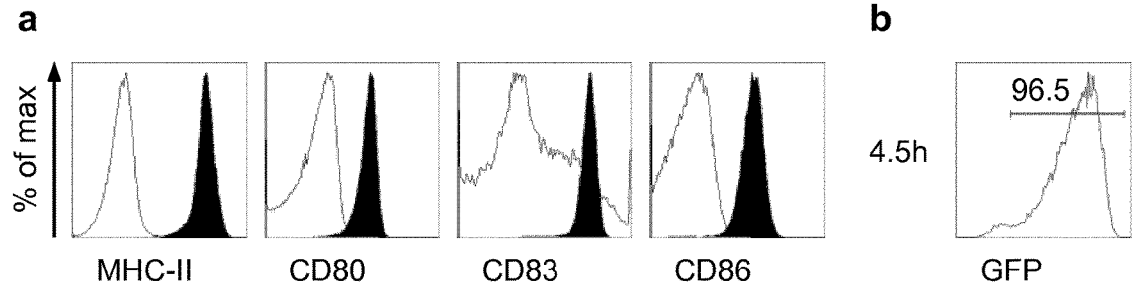

FIG. 6 mDCs express GFP from ivtRNA. mDCs were generated from plate-adherent monocytes. (a) Histograms of flow cytometry show mDCs expressing T cell activation molecules CD80, CD83 and CD86 (black lines) compared to isotype controls (grey areas). (b) Four to six hours after transfection with 15 µg antigen ivtRNA, expression of GFP was measured. Percentages of GFP$^+$ DCs are indicated.

Figure 7:
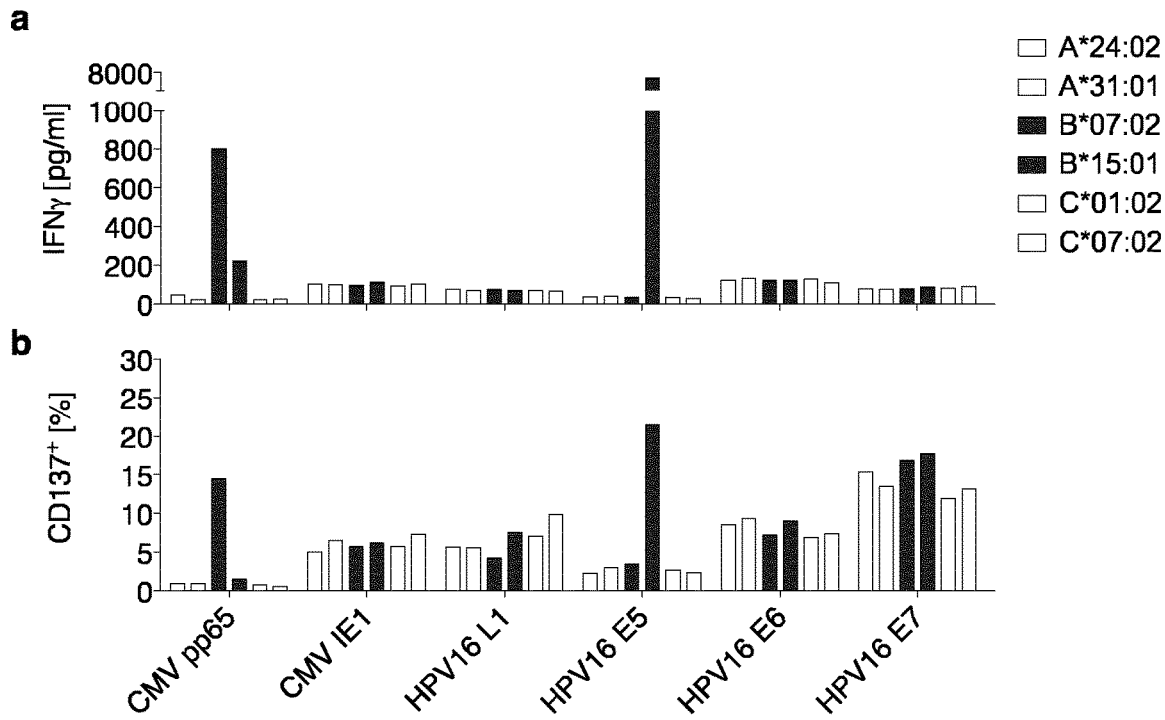

FIG. 7 Screening for virus-specific T cells. T cells, which had been stimulated antigen-specifically with autologous mDCs, were cocultured with the six corresponding single MHC I-expressing K562 cells of the MHC cell library. (a) Supernatant of the coculture was tested for IFNγ release with ELISA. (b) Cells from the same well were analyzed by flow cytometry to determine percentages of CD137$^+$ of CD8$^+$ T cells.

Figure 8:
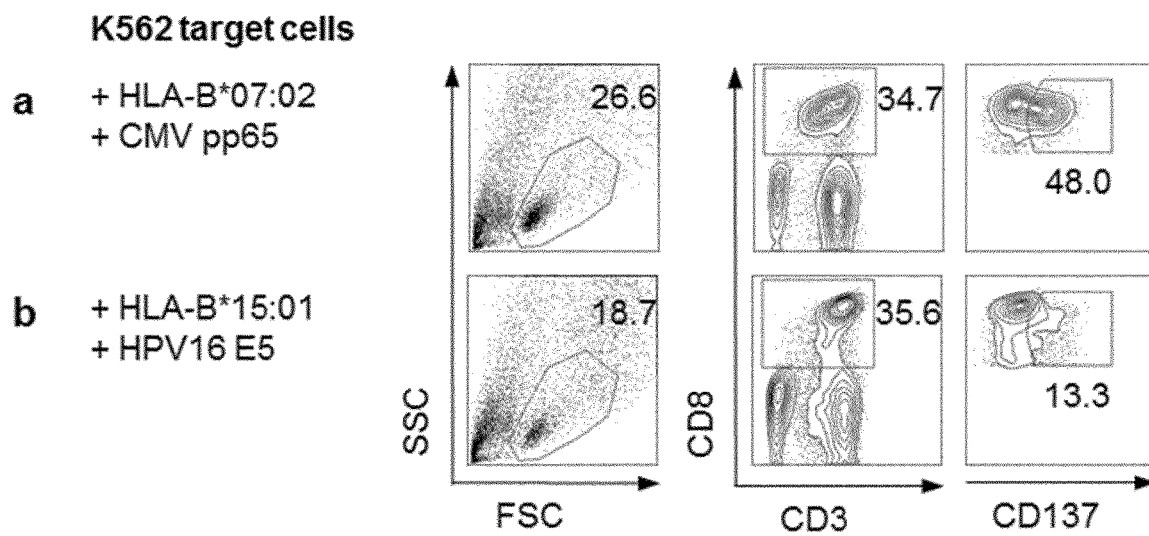

FIG. 8 FACS-sorting of virus-specific T cells. (a) T cells, which showed reactivity to pp65 (FIG. 7b), were cocultured with pp65-transfected HLA-B*07:02-expressing K562 cells of the MHC cell library. (b) E5-reactive T cells (FIG. 7b) were cocultured with E5-transfected HLA-B*15:01-expressing K562 cells of the MHC cell library. Single lymphocytes of both cocultures were gated in the FSC/SSC and CD137-expressing cells of CD8$^+$ cells were FACS-sorted for subsequent TCR analysis.

Figure 9:
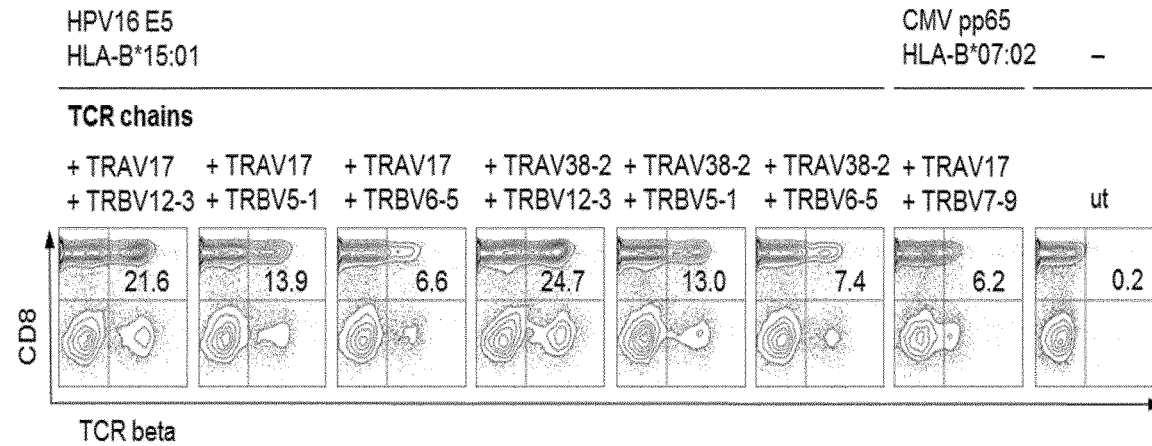

FIG. 9 Expression and functional analysis of TCR alpha and TCR beta chain combinations. (a) TCR alpha and TCR beta chain combinations were retrovirally expressed in PBMCs of healthy donors. Transgenic TCR expression in T cells was measured by flow cytometry after antibody staining for CD8 and the murine constant TCR beta chain segment. Untransduced (ut) T cells were used as a negative control. Result is representative for two independent experiments with different PBMC donors. (b) T cells transduced with the different TCR alpha and TCR beta chain combinations were cocultured with antigen (HPV16 E5 or CMV pp65)-transfected K562-B*15:01 and K562-B*07:02 target cells, respectively. IFNγ release of TCR alpha/TCR beta-transduced T cells was measured by ELISA. Results are shown as mean+/−SEM of duplicates.

Figure 10:
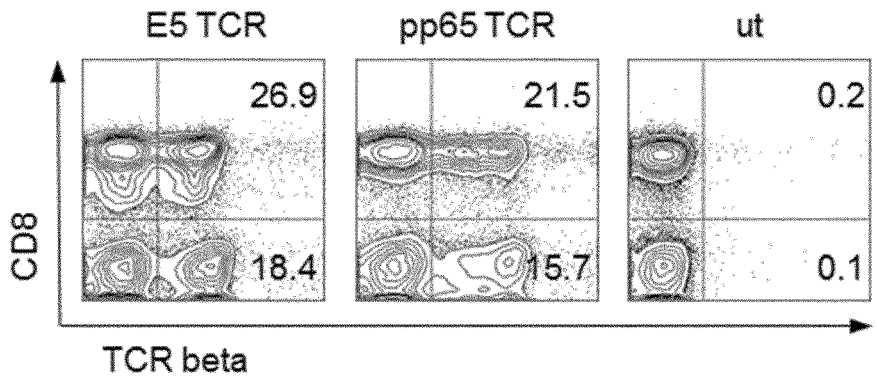

FIG. 10 Generation of TCR gene-modified PBMCs with optimized TCR transgene cassettes. Retroviral transduction of PBMCs with TCR transgene cassettes was performed. Transduction rates were assessed by antibody staining of the murine TRBC followed flow cytometric analysis. Results are representative for experiments with PBMCs from two different donors (ut, untransduced PBMCs).

Figure 11:
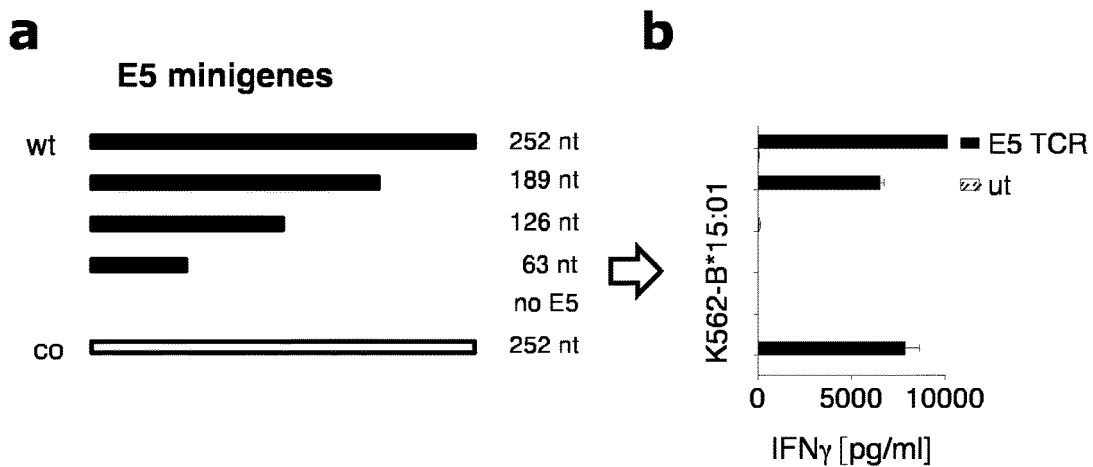

FIG. 11 Mapping of the antigenic sequence of HPV16 E5 (a) Full-length E5 wild type (wt) (252 nt), E5 codon-optimized (co) (252 nt) and 3' truncated minigene versions (63-189 nt) of E5 wt were fused to an IRES-mCherry marker, cloned into the MP71 retroviral vector and expressed in K562-B*15:01 target cells. Indicated is the length of the gene sequences starting with A of the ATG start codon. (b) TCR E5-transduced T cells were cocultured for 18 h with K562-B*15:01 target cells carrying one of the E5 gene versions. IFNγ release was determined by ELISA. Results are shown as mean+/−SEM of duplicates.

Figure 12:
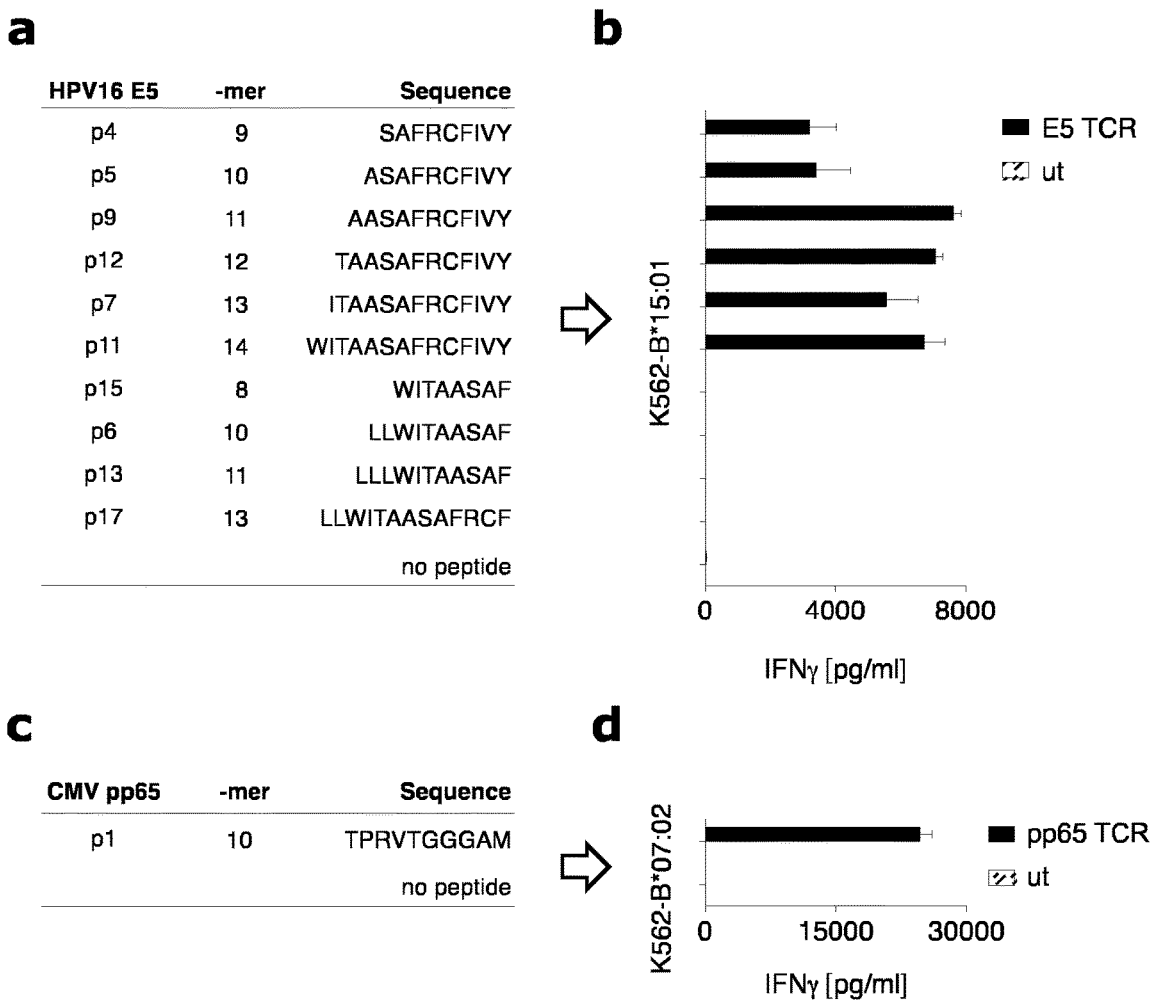

FIG. 12 Epitope mapping of the HPV16 E5-specific TCR and the CMV pp65-specific TCR. (a) HPV16 E5 epitopes predicted by IEDB as potential epitopes presented on HLA-B*15:01 were clustered according to sequence similarities. The first row (p4-p17) (SEQ ID NOs: 1, 49-61) indicates the rank of peptides in the epitope prediction (Table 2). The second row (-mer) denotes the peptide length. (b) E5 TCR-transduced PBMCs were cocultured with peptide-pulsed K562-B*15:01 target cells and IFNγ release was determined by ELISA. Untransduced (ut) T cells were used as a negative control. (c) CMV pp65 peptide p1 (SEQ ID NO: 10) represents a previously described epitope of pp65 presented on HLA-B*07:02(66,67). (d) Pp65 TCR-transduced PMBCs were cocultured with pp65 p1-pulsed K562-B*07:02 target cells. IFNγ release was measured by ELISA. All ELISA results are shown as mean+/−SEM of duplicates.

EXAMPLES 1.1 Generation of an MHC Vector Library

Genes for common MHC I alleles were cloned into the γ-retroviral vector MP71 (68-70) to first generate an MHC vector library, to generate single-MHC-expressing K562 cells (23), which were used as artificial APCs comprising the MHC cell library. Allelic versions of HLA-A, -B or -C genes are highly polymorphic. Sequences are open access at the IMGT/HLA database. However, the 5' and 3' ends of different types have high sequence similarities, making it challenging to PCR amplify one specific HLA gene from a cells' cDNA. To overcome this problem, cDNA was generated from lymphoblastoid cells (LCL) obtained from the International Histocompatibility Workshop, which were homozygous for the desired HLA-A, -B and -C alleles to enable efficient gene amplification by PCR. Amplified HLA fragments were fused to an IRES-GFP or IRES-CFP expression marker and cloned into the retroviral expression vector MP71 (FIG. 1).

1.2 Generation of MHC Cell Library

The erythroleukemic cell line K562 (20) was used as artificial APC scaffold for the generation of the MHC cell library. K562 cells lack endogenous expression of MHC class I molecules though expressing β-2 microglobulin, one ubiquitous component of functional MHC complexes. However, upon transfection with an MHC class I α-chain allele, the cells can be shown to possess a functional antigen processing machinery with MHC surface expression, thereby making K562 an attractive scaffold for the generation of artificial APCs (19,23,24). Stable transduction of K562 cells with single HLA alleles was conducted using the MP71 retroviral vector-based HLA library. Production of retroviral supernatant in 293T packaging cells and transduction was performed as described (72) and resulted in GFP- or CFP-expressing populations, as was confirmed by flow cytometric analysis. Functional assembly and surface expression of MHC complexes was indicated by MHC class I antibody staining of GFP- or CFP-positive cell populations (FIG. 2). All HLA alleles transduced in K562 cells were expressed at the cell surface. For later analysis of isolated TCRs, panels of K562 cells were generated covering all of the six MHC class I alleles of the original T cell donor.

1.3 Antigen Expression in the MHC Cell Library

To use K562 cells of the MHC cell library as artificial APCs, single-MHC-expressing K562 cells were transduced with the retroviral vector MP71 to stably express antigenic constructs in the context of a single MHC allele. Retroviral transduction was performed as described (71). Antigen expression in K562 cells allowed for endogenous processing and presentation of epitopes in the context of single MHC alleles. Many antigens (HPV16 E5, E6 and L1, CMV pp65 and IE-1) could not be detected readily by intracellular FACS staining. Furthermore, antibodies were not available for truncated antigens of HPV16 E5 (minigene constructs), which were used for epitope mapping, as well as mutated nucleotide sequences. Thus, all antigens were fused to an IRES-mCherry marker to indirectly confirm expression by flow cytometry (FIG. 3).

A second strategy to express antigenic sequences in target cells was to transfect ivtRNA via electroporation. Therefore, antigen sequences were cloned into expression vectors to enable T7 promoter-dependent generation of ivtRNA and subsequent polyadenylation using mMessage mMachine and poly(A) kits from Ambion (Life Technologies). Electroporation of ivtRNA into K562 cells was performed with a BioRad GenePulser using an exponential electroporation protocol. Generally, ivtRNA encoding GFP was used as a control for electroporation efficiency. FIG. 4 shows that HLA-transduced K562 cells expressed GFP after ivtRNA electroporation.

1.4 Induction of Antigen-Specific T Cell Response by Target Cells of MHC Cell Library In the previous experiments, it was shown that HLA-transduced K562 cells of the MHC cell library express a defined antigen after retroviral transduction or after transfection with antigen ivtRNA. The next step was to test the capacity of the MHC cell library to endogenously process and present epitopes to induce antigen-specific T cell responses. It has been described that HLA antigen-specific stimulation of T cells via the TCR leads to the upregulation of the early activation marker CD137 (32-34).

For this, two well-characterized TCRs (B23, S51) were used, which were isolated from antigen-specific T cell clones, recognizing endogenously processed and presented epitope on HLA-B*27:05. PBMCs engineered to express the TCRs (FIG. 5a, b) were used to analyze the capacity of antigen-expressing K562 cells of the MHC cell library to activate antigen-specific T cells. T cell activation was measured by CD137 expression via flow cytometry. As shown in FIG. 5c, all TCR-engineered PBMCs expressed CD137 activation marker after 20 h of coculture with antigen ivtRNA-transfected K562-B*27:05 target cells. The amount of CD8+/CD137+ T cells was around 6% for TCR-B23-engineered T cells and 8% for TCR-S51-engineered T cells, which reflects the total amount of TCR-engineered/CD8+ T cells (FIG. 5a, b) used for the coculture. In conclusion, K562 cells endogenously processed the antigenic epitope and presented it on the transgenic HLA-B*27:05, which led to the stimulation of all antigen-specific T cells in the sample as measured by CD137 expression. Additionally, CD137 expression correlated with antigen-specific IFNγ release of TCR-transduced T cells as measured by ELISA.

2.1 Antigen-Specific Expansion of T Cells

In the following, the setup of a screening approach to detect and isolate TCRs with desired antigen specificity is described. It can be transferred to different antigens, e.g., from different viruses, or different tumor-specific antigens.

Therefore, DCs were generated and matured from plate adherent monocytes (72,73) using endotoxin-free medium. Maturation state of mature DCs (mDC) was confirmed by staining for T cell activation markers CD80, CD83 and CD86 as well as MHC II expression followed by flow cytometry (FIG. 6). Antigen ivtRNA was generated from six viral antigens (CMV pp65 and IE1, HPV16 L1, E5, E6 and E7), which represented full-length reference HPV16 and CMV wild type gene sequences as indicated in the open access UniProt database. mDCs were transfected with ivtRNA of antigens to ensure the presentation of naturally processed and presented epitopes at the cell surface (74). ivtRNA encoding GFP was used as transfection control. Expression was measured 4-6 h after transfection (FIG. 6). Antigen-expressing mDCs were used at a PBMC to DC ratio of 10:1. PBMC stimulation with DCs was performed using medium containing 10% human serum (74,75). IL-2 (20 U/ml) and IL-7 (5 ng/ml) were provided with the medium from day 2 of stimulation on to favor T cell proliferation. Three times a week IL-2 (20 U/ml) and IL-7 (5 ng/ml) was provided to the culture. Proliferating PBMCs were splitted at ratios of 1:2 to 3:4.

2.2 Screening for Virus-Specific T Cells

A second stimulation was performed 14 days after the first round of stimulation using autologous mDCs expressing one of the six viral antigens. After 28 days, the 12 T cell cultures were screened for reactivity to specific antigen-MHC combinations employing the MHC cell library (FIG. 2). Cells of the MHC cell library were transfected with antigen ivtRNA via electroporation and each T cell culture raised against one antigen was screened for reactivity to the antigen in combination with one MHC type. Contacting of the library with T cells was performed preferably 18-22 h to achieve optimal activation of antigen-specific T cells within the T cell sample. The addition of cytokines was avoided during contacting to prevent T cells from unspecific activation. IFNγ release of antigen-specific T cells was measured by ELISA. Further, the T cells in the coculture were analyzed for expression of CD137 by flow cytometry (33).

T cells showed specific reactivity to pp65 and E5 in combination with HLA-B*07:02 and HLA-B*15:01, respectively. Antigen-MHC-specific T cell reactivity could be measured by release of IFNγ and upregulation of CD137 at the T cell surface. Thus, combining cytokine release ELISA and flow cytometric analysis of T cell activation marker represents a robust two-method read out system for detecting antigen-MHC-specific T cell responses.

2.3 Sorting of Virus-Specific T Cells to Analyze the TCR Repertoire

T cells, which showed specific responses to one antigen-MHC combination in both assays, were selected for FACS sorting to analyze the TCR repertoire. T cells, which were expanded with CMV pp65, were cocultured with pp65-transfected K562-B*07:02 target cells, and CD137+ T cells were sorted from the culture. Nearly half of the CD8+ T cells were CD137+ in this setting. Thirteen percent of CD8+ T cells expressed CD137 upon coculture with HPV16 E5-transfected K562-B*15:01 target cells.

After sorting of antigen-MHC-specific T cells, RNA was isolated and cDNA was generated using the SMARTer RACE cDNA amplification kit (Clontech) for 5'-RACE PCR of TCR alpha and beta genes. The PCR amplification generated TCR alpha and beta gene fragments, which quantitatively represented the amount of each T cell clonotype in the FACS-sorted T cell sample. PCR products of TCR alpha and beta gene fragments were ligated into sequencing vectors using the TOPO® cloning system (Invitrogen, Life Technologies), transformed into bacteria and grown on plates containing selective medium. Each bacterial colony was regarded as containing one sequencing vector with one PCR TCR alpha or beta gene fragment. Vector DNA preparations of numerous bacterial colonies were followed by sequencing of vector inserts (TCR alpha or beta gene fragments). Sequencing results of each bacterial colony were analyzed by using the web-based IMGT/V-Quest. Frequencies of identical TCR alpha or beta chains reflected the proportion of identical T cell clonotypes within the FACS-sorted T cell sample. Next, frequency matching of TCR alpha and beta chains was performed to reconstitute functional TCRs, which had accounted for antigen-MHC-specific IFNγ release and CD137 upregulation.

TCR analysis revealed TRAV17 and TRAV38-2 chains each to be present in nearly 40% of all T cells sorted upon response to HPV16 E5 and HLA-B*15:01. Three TCR beta variable chains were found to be present in 21-32% of T cells (Table 1). It was assumed that each of the two TCR alpha chains could assemble a functional E5-specific TCR with one of the three TCR beta chains. Thus, there were six possible combinations of candidate TCR alpha and TCR beta chains to assemble a functional HPV16 E5-specific TCR.

T cells sorted for reactivity to CMV pp65 and HLA-B*07:02 had one predominant TCR with a TRAV17 and a TRBV7-9 chain, both being present in about 70% of TCR alpha and TCR beta colonies, respectively (Table 1).

In sum, TCR analysis showed that CD137 sorting of antigen-MHC-specific T cells is accompanied by a strong enrichment for few predominant TCR alpha and beta chains, which appear at high frequency and which may reconstitute functional antigen-MHC-specific TCRs.

TABLE 1

TCR analysis

| MHC class I | V segment | | CDR-3 | SEQ ID NO: | Frequency | % of total |
|---|---|---|---|---|---|---|
| Antigen HPV16E5 | | | | | | |
| HLA-B*15:01 | Homsap | TRAV17*01 F | CAESEYGNKLVF | 2 | 10 | 38,5 |
| | Homsap | TRAV38-2/DV8*01 F | CAYRSWNYGQNFVF | 19 | 10 | 38,5 |
| | Homsap | TRAV8-6*02 F | CAVSEPAAGNKLTF | 20 | 2 | 7,7 |
| | Homsap | TRAV26-2*01 F | CILRGAGGTSYGKLTF | 21 | 1 | 3,8 |
| | Homsap | TRAV8-6*02 F | CAVITNAGKSTF | 22 | 1 | 3,8 |
| | Homsap | TRAV25*01 F | CAGPPSGTYKYIF | 23 | 1 | 3,8 |
| | Homsap | TRAV6*02 (F) | CALPMEYGNKLVF | 24 | 1 | 3,8 |
| | Homsap | TRBV5-1*01 F | CASSSRGHQNTGELFF | 25 | 6 | 21,4 |
| | Homsap | TRBV12-3*01 F | CASSPEGEVTGELFF | 26 | 8 | 28,6 |
| | Homsap | TRBV6-5*01 F | CASSYRQQETQYF | 6 | 9 | 32,1 |
| | Homsap | TRBV5-1*01 F | CASTLRGYTEAFF | 27 | 1 | 3,6 |
| | Homsap | TRBV5-5*02 (F) | CASSPWADSNQPQHF | 28 | 1 | 3,6 |
| | Homsap | TRBV20-1*01 F | CSAGTSGGPAYEQYF | 29 | 1 | 3,6 |
| | Homsap | TRBV27*01 F | CASSSPLADDYNEQFF | 30 | 1 | 3,6 |
| | Homsap | TRBV6-2*01 F | CASSHRRAHRAREQYF | 31 | 1 | 3,6 |
| Antigen CMV pp65 | | | | | | |
| HLA-B*07:02 | Homsap | TRAV14/DV4*01 F | CAMREGKDSSYKLIF | 32 | 2 | 8,7 |
| | Homsap | TRAV17*01 F | CATVIRMDSSYKLIF | 11 | 17 | 73,9 |
| | Homsap | TRAV8-1*01 F | CAVNRGGSNYKLTF | 33 | 1 | 4,3 |
| | Homsap | TRAV3*01 F | CAVRDIGGFKTIF | 34 | 1 | 4,3 |
| | Homsap | TRAV1-2*01 F | CALDGQKLLF | 35 | 1 | 4,3 |
| | Homsap | TRAV4*01 F | CLVGGLRGNVLHC | 36 | 1 | 4,3 |
| | Homsap | TRBV7-9*03 F | CASSLIGVSSYNEQFF | 15 | 13 | 68,4 |
| | Homsap | TRBV27*01 F | CASRLGGGNYNEQFF | 37 | 4 | 21,1 |
| | Homsap | TRBV20-1*01 F | CSASPRDRKFSGNTIYF | 38 | 1 | 5,3 |
| | Homsap | TRBV7-9*03 F | CASSSHDNQGAKSPLHF | 39 | 1 | 5,3 |

TCR alpha and TCR beta chains were amplified with TRAC- and TRBC-specific reverse primers from 5'-RACE cDNA of T cells, which had shown antigen-MHC-specific T cell responses. TCR analysis was performed with IMGT/V-Quest. V(D)J gene usage and CDR3 sequences specify identical TCR alpha or TCR beta chains. Frequencies of colonies carrying one TCR alpha or TCR beta chain are indicated. Percentage of total indicates the proportion of colonies with identical TCR alpha or TCR beta chains.

2.4 Functional Analysis of TCR Alpha and TCR Beta Chain Combinations

For transgenic expression of TCRs, each TCR alpha and TCR beta chain gene was cloned into the γ-retroviral vector MP71. Cell surface expression and functional analysis of TCRs was performed after stable transduction of PBMCs with different TCR alpha and TCR beta gene combinations.

Variable regions of predominant TCR alpha and TCR beta chain genes (TRAV and TRBV), which are responsible for peptide-MHC (pMHC) I binding, were fused to codon-optimized murine constant TCR alpha and TCR beta gene segments (mTRAC and mTRBC) to enable preferential pairing of transgenic TCR chains after retroviral transduction of T cells (39,40,71). Staining of transgenic TCRs with an antibody specific for the mTRBC was followed by flow cytometric analysis and showed that all TRA/TRB chain combinations were expressed in PBMCs (FIG. 9a). However, transduction rates of different combinations varied between 6-25%. For functional analysis, TCR-transduced T cells were tested for reactivity to K562-B*15:01 or K562-B*07:02 target cells, which were transfected via electroporation with HPV16 E5 or CMV pp65 antigen ivtRNA, respectively. Strikingly, T cells expressing TRAV17 (SEQ ID NO: 3) in combination with TRBV6-5 (SEQ ID NO: 7) recognized E5-transfected target cells, whereas none of the other five TRA/TRB combinations showed antigen-specific reactivity to E5 (FIG. 9b). Therefore, TRAV17 in combination with TRBV6-5 reconstituted a functional antigen-specific TCR. The only candidate TRA/TRB combination of CMV-reactive T cells (TRAV17 (SEQ ID NO: 12) and TRBV7-9 (SEQ ID NO: 16)) showed pp65-specific recognition of K562-B*07:02 target cells. TRA/TRB-transduced T cells showed no background reactivity to H₂O-transfected target cells (FIG. 9b), thus allowing clear identification of functional antigen-MHC-specific TCRs.

In conclusion, reconstitutions of TCRs from antigen-specific T cell clonotypes were achieved through the combination of TRA and TRB chains, which were found at high frequencies in FACS-sorted T cell samples. Screening, detection and isolation of TCRs with desired antigen specificity could be achieved by this approach, which was based on the use of the MHC cell library.

2.5 Optimization of HPV- and CMV-Specific TCRs for Transgenic Expression in PBMCs To increase efficiency of transgenic TCR expression, several optimizations of TCR transgene sequences were applied (71). TRA and TRB chain sequences were codon-optimized and human TRAC and TRBC gene segments were replaced by their murine counterparts to increase preferential binding of transgenic TCR chains and to reduce pairing with endogenous TCR chains expressed by recipient T cells (SEQ ID NO: 5, 9, 14, 18). The optimized TRB gene was then linked via a P2A element to the TRA genes and resulting single TCR transgene cassettes (E5-specific: SEQ ID NO: 40, pp65-specific: SEQ ID NO: 41) were molecularly cloned into the γ-retroviral vector MP71. Retroviral particles carrying the optimized TCR transgene cassettes were generated via a three-plasmid transfection of 293T cells and donor PBMCs were stably transduced with retroviral particles encoding the TCRs (70). TCR gene-modified T cells within the PBMC sample were analyzed by flow cytometry after antibody staining of the transgenic murine TRBC. TCR transduction rates of 45% for the E5-specific TCR (TRAV17+TRBV6-5, SEQ ID NO: 40) and 37% for pp65-specific TCR (TRAV17+TRBV7-9, SEQ ID NO: 41) could be achieved in PBMCs, whereby 27% and 22%, respectively, were positive for CD8 and the transgenic TCR. In conclusion, transgenic TCR expression could be improved markedly from 6-7% when using the non-optimized TRA and TRB single chain transgene cassettes, which were used to reconstitute functional TCRs, to approximately 40% when using the optimized TCR transgene cassettes.

2.6 Epitope Mapping of the HPV16 E5-Specific TCR

After detection of T cell clonotypes recognizing immunogenic antigen-MHC combination without prior knowledge of immunogenic epitopes, epitope mapping was performed to reveal the exact peptide sequence within the antigenic HPV16 E5 protein, which is recognized by the E5-specific TCR. The HPV16 E5-specific TCR composed of TRAV17 and TRBV6-5 sequences was an unique TCR, which has not been described before. To map the antigenic sequence recognized by the TCR, 3'-truncated minigene versions of HPV16 E5 generated by PCR with primers amplifying the respective gene region of interest. E5 minigenes were cloned into the retroviral vector MP71 and stably transduced into K562-B*15:01 target cells (FIG. 11a). T cells transduced with the optimized E5-specific TCR gene cassette recognized target cells carrying the full-length E5 and the 189 nt E5 minigene sequence but not 126 and 63 nt E5 minigenes as indicated by IFNγ release (FIG. 11b). Furthermore, E5 TCR-transduced T cells released IFNγ irrespective of whether the target cells harbored E5wt or E5co gene sequences (FIG. 11b). In conclusion, the HPV16 E5 TCR was specific for an epitope within the E5 protein region between amino acid 42-63.

To narrow down candidate epitopes that may be the target of E5-specific TCR recognition, in silico epitope prediction was performed using the web-based IEDB T cell epitope combined predictor, which integrates predictions of proteasomal cleavage, TAP transport, ER processing and MHC class I binding. Integrated epitope prediction was performed including 8-14-mer peptides in one analysis. Epitope prediction results were calculated as total score, which can be interpreted as the probability of a given peptide to be processed and presented on an MHC molecule at the cell surface. Table 2 includes all epitopes (p1-p17) of the prediction with a positive total score using constitutive proteasome prediction. In contrast to DCs, K562 cells express a constitutive proteasome, which resembles proteasomes expressed in tumor cells (76). All epitopes, which were not expressed from amino acid sequence 42-63 of HPV16 E5 were excluded from further analysis. Surprisingly, the top three predicted epitopes (p1-p3) had to be discarded.

TABLE 2

Epitope prediction of HPV16 E5

| # | Pos. | -mer | Sequence | Affinity to MHC [nM] | Total score | SEQ ID NO |
|---|------|------|----------|----------------------|-------------|-----------|
| p1 | 28 | 12 | LIRPLLLSVSTY | 42,98 | 0,70 | 42 |
| p2 | 27 | 13 | LLIRPLLLSVSTY | 39,49 | 0,67 | 43 |
| p3 | 72 | 9 | FLIHTHARF | 32,60 | 0,60 | 44 |

TABLE 2-continued

Epitope prediction of HPV16 E5

| # | Pos. | -mer | Sequence | Affinity to MHC [nM] | Total score | SEQ ID NO |
|---|------|------|----------|----------------------|-------------|-----------|
| p4 | 55 | 9 | SAFRCFIVY | 97,77 | 0,60 | 1 |
| p5 | 54 | 10 | ASAFRCFIVY | 102,30 | 0,58 | 45 |
| p6 | 48 | 10 | LLWITAASAF | 39,05 | 0,58 | 46 |
| p7 | 51 | 13 | ITAASAFRCFIVY | 79,80 | 0,51 | 47 |
| p8 | 32 | 8 | LLLSVSTY | 63,70 | 0,38 | 48 |
| p9 | 53 | 11 | AASAFRCFIVY | 143,79 | 0,36 | 49 |
| p10 | 55 | 14 | SAFRCFIVYIIFVY | 138,79 | 0,36 | 50 |
| p11 | 50 | 14 | WITAASAFRCFIVY | 144,35 | 0,32 | 51 |
| p12 | 52 | 12 | TAASAFRCFIVY | 149,57 | 0,28 | 52 |
| p13 | 47 | 11 | LLLWITAASAF | 70,87 | 0,25 | 53 |
| p14 | 11 | 9 | LLACFLLCF | 119,99 | 0,10 | 53 |
| p15 | 50 | 8 | WITAASAF | 108,63 | 0,08 | 55 |
| p16 | 73 | 8 | LIHTHARF | 116,82 | 0,05 | 56 |
| p17 | p11 | 13 | LLWITAASAFRCF | 169,11 | 0,00 | 57 |

Integrated MHC class I epitope prediction (IEDB) was used to rank the likelihood
of candidate target epitopes (p1-17) for the HPV16 E5-specific TCR. Depicted is
the position of the first amino acid of predicted peptides within the full-
length HPV16 E5 protein (Pos.), peptide length (-mer), amino acid sequence,
predicted binding affinity to HLA-B*15:01 and the SEQ ID NO. The algorithm
uses a combined total score (arbitrary units), which integrates predictions for
proteasomal cleavage, TAP transport and MHC (HLA-B*15:01) binding affinity. The
table shows only peptides with a total score higher than zero. The higher the
total score, the higher the efficiency of a peptide to be processed and
presented at the cell surface. Epitopes in bold print were translated from
126-189 nt sequence of E5. Epitopes in italics were recognized by the TCR.

The result of the integrated epitope prediction of HPV16 E5 is listed in Table 2. The best predicted epitope was ranked first. Peptides encoded within amino acid sequence 42-63 are shown in bold print. These ten candidate epitopes were clustered according to sequence similarities (FIG. 12a) and peptides were exogenously loaded on K562-B*15:01 target cells. E5 TCR-transduced PBMCs specifically recognized HPV16 E5 epitope p4 (SAFRCFIVY, SEQ ID NO: 1). Additionally, the TCR clearly recognized all N-terminally elongated derivatives of SAFRCFIVY (SEQ ID NO: 1) including 12-, 13- and 14-mers conferring unconventional peptide lengths for MHC I (FIG. 12b). HLA-B*15:01 may tolerate binding of peptides which protrude at the N-terminus. In contrast, none of the other peptides was recognized, although peptide p6 and p13 were predicted to have higher binding affinities to HLA-B*15:01 than p4.

In sum, integrated epitope prediction facilitated mapping of the exact epitope recognized by the E5-specific TCR. However, the algorithm could not predict the immunogenic epitope, and mapping of antigenic sequence with truncated minigenes of E5 was necessary prior to epitope prediction.

The isolated TRAV17 and TRBV7-9 sequences resembled a CMV-specific TCR. TCR sequences specific for CMV pp65 and restricted to HLA-B*07:02 have been published with one to five amino acids difference in the CDR3 regions (66,67) (Table 1). These TCRs had been reported to recognize the TPRVTGGGAM (SEQ ID NO: 10) 10-mer epitope of CMV pp65 when presented on HLA-B*07:02. Here, pp65 TCR-transduced PBMCs were cocultured with K562-B*07:02 target cells loaded with CMV pp65-derived epitope p1 (TPRVTGGGAM, SEQ ID NO: 10) (FIG. 12a). Indeed, TCR-transduced T cells recognized p1-pulsed target cells and released IFNγ (FIG. 12b). pp65 TCR-transduced PBMCs were specific for p1, despite sequence differences in the CDR3 region compared to previously published pp65-B*07:02-specific TCRs.

In summary, this approach enabled the identification of a novel immunogenic HPV16 E5 epitope and its corresponding TCR and of an immunodominant CMV pp65 epitope and its corresponding TCR. Both TCRs were specific for endogenously processed epitopes and reflected the T cell response caused by only one T cell clonotype in the initial MHC cell library-based screening. Thus, an unbiased screening of natural T cell responses and the identification of TCRs rapidly after antigen-specific in vitro stimulation is possible with the method of the invention, without prior knowledge of the epitope, thereby avoiding limitations of epitope prediction programs to predict functional T cell responses to a defined antigen and avoiding resource-intensive and unfavorable T cell clone culture. This approach can also be applied to TILs or tissue-resident T cells and screenings can be extended to further pathogen-derived and tumor-specific antigens as well as any antigen to be targeted by a TCR.

REFERENCES

1. Schumacher T N M. Nat Rev Immunol 2002; 2(July):512-9.
2. Vonderheide R H, June C H. Immunol Rev. 2014 January; 257(1):7-13.
3. Restifo N P, Dudley M E, Rosenberg S a. Nat Rev Immunol 2012 April; 12(4):269-81.
4. Hinrichs C S, Rosenberg S a. Immunol Rev. 2014 January; 257(1):56-71.
5. Han A, Glanville J, Hansmann L, et al. Nat Biotechnol. 2014 July; 32(7):684-92.
6. Yee C. Immunol Rev. 2014 January; 257(1):250-63.
7. Iezzi G, Karjalainen K, Lanzavecchia A. Immunity. 1998; 8:89-95.
8. Ho W Y, Nguyen F I N, Wolfl M, et al. J Immunol 2006; 310:40-52.
9. Altman J D, Moss P A H, Goulder P J R, et al. Science (80-). 1996; 274(5284):94-6.
10. Hadrup S R, Bakker A H, Shu C J, et al. Nature. 2009; 6(7):520-6.
11. Knabel M, Franz T J, Schiemann M, et al. Nat Med. 2002; 8(6):631-7.
12. Bakker A H, Schumacher T N M. Curr Opin Immunol. 2005; 17:428-33.
13. Davis M M, Altman J D, Newell E W. Nat Rev Immunol 2011; 11(8):551-8.
14. Pascolo B S, Bervas N, Ure J M, et al. J Exp Med. 1997; 185(12).
15. Boucherma R, Kridane-Miledi H, Bouziat R, et al. J Immunol. 2013 Jul. 15; 191(2):583-93.
16. Li L-P, Lampert J C, Chen X, et al. Nat Med 2010 September; 16(9):1029-34.
17. Fontana R, Bregni M, Cipponi A, et al. Blood. 2009; 113(8):1651-61.
18. Lamers C H J, Willemsen R, Elzakker P Van, et al. Blood. 2011; 117(1):72-83.
19. Zeng W, Su M, Anderson K S, et al. Immunobiology. 2014 August; 219(8):583-92.
20. Lozzio C B, Lozzio B B. Blood. 1975 March; 45(3):321-34.
21. Drew S I, Terasaki P I, Billing R J, et al. Blood. 1977; 49:715-8.
22. Boegel S, Lower M, Bukur T, et al. Oncoimmunology. 2014; 3(8):37-41.
23. Britten C M, Meyer R G, Kreer T, et al. J Immunol Methods. 2002; 259:95-110.
24. Suhoski M M, Golovina T N, Aqui N A, et al. Mol Ther. 2007; 15(5):981-8.
25. Klein E, Ben-Bassat H, Neumann H, et al. Int J Cancer. 1976; 18:421-31.
26. Bai X, Hosler G, Rogers B B, et al. Clin Chem. 1997; 43(10):1843-9.
27. Anderson K S, Zeng W, Sasada T, et al. Cancer Immunol Immunother. 2013; 60(6):857-67.
28. Latouche J, Sadelain M. Nat Biotechnol. 2000; 18(February).
29. Hasan A N, Kollen W J, Trivedi D, et al. J Immunol 2009; 183:2837-50.
30. Butler M O, Ansén S, Tanaka M, et al. Int Immunol. 2010 November; 22(11):863-73.
31. McKinney D M, Southwood S, Hinz D, et al. Immunogenetics. 2013 May; 65(5):357-70.
32. Watanabe K, Suzuki S, Kamei M, et al. Int J Hematol. 2008 October; 88(3):311-20.
33. Wolff M, Kuball J, Ho W Y, et al. Blood. 2007 Jul. 1; 110(1):201-10.
34. Wolfl M, Kuball J, Eyrich M, et al. Cytometry A. 2008; 73(11):1043-9.
35. Manz R, Assenmacher M, Pflugert E, et al. Proc Natl Acad Sci. 1995; 92(March):1921-5.
36. Becker C, Pohla H, Frankenberger B, et al. Nat Med. 2001; 7(10):1159-62.
37. Brosterhus H, Brings S, Leyendeckers H, et al. Eur J Immunol 1999; 29:4053-9.
38. Linnemann C, Heemskerk B, Kvistborg P, et al. Nat Med. 2013 Oct. 13; 19(11):1534-41.
39. Cohen C J, Zhao Y, Zheng Z, et al. Cancer Res. 2006; 66:8878-86.
40. Sommermeyer D, Uckert W. J Immunol 2010 Jun. 1; 184(11):6223-31.
41. Cohen C J, Li Y F, El-Gamil M, et al. Cancer Res. 2007; 67(8):3898-903.
42. Kuball J, Dossett M L, Wolff M, et al. Blood. 2007; 109(6):2331-8.
43. Zur Hausen H. Nat Rev Cancer. 2002 May; 2(5):342-50.
44. Walboomers J M, Jacobs M V, Manos M M, et al. J Pathol. 1999; (May):12-9.
45. Woodman C B J, Collins S I, Young L S. Nat Rev Cancer. 2007 January; 7(1):11-22.
46. Moody C A, Laimins L A. Nat Rev Cancer. 2010; 10:550-60.
47. Straight S W, Hinkle P M, Jewers R J, et al. J Virol. 1993; 67(8):4521-32.
48. Halbert C L, Galloway D a. J Virol. 1988 March; 62(3):1071-5.
49. Chan J L, Tsao Y P, Liu D W, et al. J Biomed Sci. 2001; 8:206-13.
50. Schmitt M, Dalstein V, Waterboer T, et al. Cancer Res. 2010 Jan. 1; 70(1):249-56.
51. Tang K-W, Alaei-Mahabadi B, Samuelsson T, et al. Nat Commun. 2013 Oct. 1; 4:2513.

52. Kenter G G, Welters M J P, Valentijn A R P M, et al. N Engl J Med. 2009 November; 361(19):1838-47.
53. Stern P L, van der Burg S H, Hampson I N, et al. Vaccine. 2012; 30 Suppl 5:F71-82.
54. Reddehase M J. Nat Rev Immunol 2002 November; 2(11):831-44.
55. Ghazi A, Ashoori A, Hanley P, et al. J Immunother. 2012; 35(2):159-68.
56. Schuessler A, Smith C, Beagley L, et al. Cancer Res. 2014 Jul. 1; 74(13):3466-76.
57. Wick W, Platten M. Neuro Oncol. 2014; 16(3):332-3.
58. Söderberg-Naucler C, Rahbar A, Stragliotto G. N Engl J Med. 2013 Sep. 5; 369(10):984-5.
59. Gonzalez-Galarza F F, Christmas S, Middleton D, et al. Nucleic Acids Res. 2011; 39(November 2010):913-9.
60. Chervin A S, Aggen D H, Raseman J M, et al. J Immunol Methods. 2008; 339(2):175-84.
61. Robbins P F, Li Y F, E I-Gamil M, et al. J Immunol 2008; 180:6116-31.
62. Linette G P, Stadtmauer E A, Maus M V, et al. Blood. 2013; 122(6):863-72.
63. Liddy N, Bossi G, Adams K J, et al. Nat Med. 2012 May 6; 18(6).
64. Einsele H, Roosnek E, Rufer N, et al. Blood. 2002; 99(11):3916-22.
65. Reusser P, Riddell S R, Meyers J D, et al. Blood. 1991; 78:1373-80.
66. Dössinger G, Bunse M, Bet J, et al. PLoS One. 2013 January; 8(4):e61384.
67. Khan N, Shariff N, Cobbold M, et al. J Immunol 2002; 169.
68. Schambach A, Wodrich H, Hildinger M, et al. Mol Ther. 2000; 2(4):435-45.
69. Baum C, Hegewisch-becker S, Eckert H, et al. J Virol. 1995; 69(12):7541-7.
70. Engels B, Cam H, Schiller T, et al. Hum Gene Ther. 2003 Aug. 10; 14(12):1155-68.
71. Leisegang M, Engels B, Meyerhuber P, et al. J Mol Med. 2008; 86(5):573-83.
72. Bürdek M, Spranger S, Wilde S, et al. J Transl Med. 2010 January; 8:90.
73. Spranger S, Javorovic M, Bürdek M, et al. J Immunol 2010 Jul. 1; 185(1):738-47.
74. Wilde S, Sommermeyer D, Frankenberger B, et al. Blood. 2009 September; 114(10):2131-9.
75. Spranger S, Jeremias I, Wilde S, et al. Blood. 2012; 119:3440-9.
76. Melief C J M. Immunity 2008 Sep. 19; 29(3):372-83.

---

The invention claimed is:

1. A method for preparing a nucleic acid encoding the TRA and TRB of a TCR construct specific for an immunodominant epitope from a defined antigen presented on a WIC, comprising
   (a) stimulating T cells isolated from a healthy donor with professional antigen presenting cells presenting epitopes of said defined antigen, to enrich antigen-specific T cells; and
   (b) contacting said antigen-specific T cells enriched in step a with a library of cells, wherein each cell expresses a single MHC allele, wherein the library comprises cells expressing all MHC I alleles present in the donor, and wherein the cells of said library present epitopes of said defined antigen; wherein T cells expressing TCR specific for said epitopes become activated T cells; and
   (c) selecting T cells activated by said contact in step b, preferably, based on an activation marker expressed by said activated T cells; and
   (d) isolating the nucleic acids encoding the TCR alpha and TCR beta chains of the TCR of said activated T cells selected in step c.

2. The method of claim 1, wherein the library of cells comprises MHC I-expressing K562 cells.

3. The method of claim 1, wherein the method further comprises optimizing the sequence of the nucleic acid of step d.

4. A method for preparing a T cell expressing a TCR construct specific for an epitope from a defined antigen presented on a MHC, comprising carrying out the method of claim 1, and expressing said nucleic acids encoding the TRA and TRB in a T cell.

5. A method for identifying an epitope capable of being presented by a MHC in a defined antigen, comprising carrying out steps (a)-(d) of claim 1 and identifying the epitope capable of activating T cells transfected with nucleic acids encoding the isolated TRA and TRB constituting the TCR construct, wherein the epitope is optionally prepared in peptide or nucleic acid form.

6. The method of claim 3, further comprising optimizing codon usage of the TRA and TRB.

7. The method of claim 3, further comprising combining human variable regions with murine constant regions or minimal murine constant regions.

* * * * *

UNITED STATES PATENT AND TRADEMARK OFFICE
CERTIFICATE OF CORRECTION

| | |
|---|---|
| PATENT NO. | : 11,001,830 B2 |
| APPLICATION NO. | : 15/558765 |
| DATED | : May 11, 2021 |
| INVENTOR(S) | : Felix Lorenz et al. |

It is certified that error appears in the above-identified patent and that said Letters Patent is hereby corrected as shown below:

In the Specification

Column 1, Lines 20-21, "said TCR immunogenic" should be corrected to read "said TCR. Immunogenic"

Column 5, Line 42, "of an MHC I a chain" should be corrected to read "of a MHC I α chain"

Column 9, Line 54, "immune dominace TCR" should be corrected to read "immune dominace. TCR"

Column 24, in the last sentence in the legend to Table 2, "sequence of ES" should be corrected to read "sequence of E5"

In the Claims

Column 73, Claim 1, Lines 15-16, "antigen presented on a WIC, comprising" should be corrected to read "antigen presented on a MHC, comprising"

Signed and Sealed this
Thirty-first Day of May, 2022

Katherine Kelly Vidal
*Director of the United States Patent and Trademark Office*

SEQUENCE LISTING

```
<160> NUMBER OF SEQ ID NOS: 71

<210> SEQ ID NO 1
<211> LENGTH: 9
<212> TYPE: PRT
<213> ORGANISM: Alphapapillomavirus 9
<220> FEATURE:
<223> OTHER INFORMATION: HPV16 E5 epitope restricted to HLA-B*15:01

<400> SEQUENCE: 1

Ser Ala Phe Arg Cys Phe Ile Val Tyr
1               5

<210> SEQ ID NO 2
<211> LENGTH: 12
<212> TYPE: PRT
<213> ORGANISM: Artificial Sequence
<220> FEATURE:
<223> OTHER INFORMATION: CDR3 of TRA specific for E5 epitope

<400> SEQUENCE: 2

Cys Ala Glu Ser Glu Tyr Gly Asn Lys Leu Val Phe
1               5                   10

<210> SEQ ID NO 3
<211> LENGTH: 131
<212> TYPE: PRT
<213> ORGANISM: Artificial Sequence
<220> FEATURE:
<223> OTHER INFORMATION: variable region of TRA specific for E5 epitope,
      TRAV17

<400> SEQUENCE: 3

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45
```

```
Ile Asn Asn Leu Gln Trp Tyr Arg Gln Asn Ser Gly Arg Gly Leu Val
 50                  55                  60

His Leu Ile Leu Ile Arg Ser Asn Glu Arg Glu Lys His Ser Gly Arg
 65                  70                  75                  80

Leu Arg Val Thr Leu Asp Thr Ser Lys Lys Ser Ser Ser Leu Leu Ile
                 85                  90                  95

Thr Ala Ser Arg Ala Ala Asp Thr Ala Ser Tyr Phe Cys Ala Glu Ser
                100                 105                 110

Glu Tyr Gly Asn Lys Leu Val Phe Gly Ala Gly Thr Ile Leu Arg Val
                115                 120                 125

Lys Ser Tyr
        130
```

<210> SEQ ID NO 4
<211> LENGTH: 267
<212> TYPE: PRT
<213> ORGANISM: Artificial Sequence
<220> FEATURE:
<223> OTHER INFORMATION: TRA specific for E5 epitope, optimized

<400> SEQUENCE: 4

```
Met Glu Thr Leu Leu Gly Val Ser Leu Val Ile Leu Trp Leu Gln Leu
 1                   5                  10                  15

Ala Arg Val Asn Ser Gln Gln Gly Glu Glu Asp Pro Gln Ala Leu Ser
                 20                  25                  30

Ile Gln Glu Gly Glu Asn Ala Thr Met Asn Cys Ser Tyr Lys Thr Ser
                 35                  40                  45

Ile Asn Asn Leu Gln Trp Tyr Arg Gln Asn Ser Gly Arg Gly Leu Val
 50                  55                  60

His Leu Ile Leu Ile Arg Ser Asn Glu Arg Glu Lys His Ser Gly Arg
 65                  70                  75                  80

Leu Arg Val Thr Leu Asp Thr Ser Lys Lys Ser Ser Ser Leu Leu Ile
                 85                  90                  95

Thr Ala Ser Arg Ala Ala Asp Thr Ala Ser Tyr Phe Cys Ala Glu Ser
                100                 105                 110

Glu Tyr Gly Asn Lys Leu Val Phe Gly Ala Gly Thr Ile Leu Arg Val
                115                 120                 125

Lys Ser Tyr Ile Gln Asn Pro Glu Pro Ala Val Tyr Gln Leu Lys Asp
        130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Thr Val Leu Asp Met Lys Ala Met Asp Ser Lys Ser Asn Gly Ala
                180                 185                 190

Ile Ala Trp Ser Asn Gln Thr Ser Phe Thr Cys Gln Asp Ile Phe Lys
                195                 200                 205

Glu Thr Asn Ala Thr Tyr Pro Ser Ser Asp Val Pro Cys Asp Ala Thr
                210                 215                 220

Leu Thr Glu Lys Ser Phe Glu Thr Asp Met Asn Leu Asn Phe Gln Asn
225                 230                 235                 240

Leu Ser Val Met Gly Leu Arg Ile Leu Leu Leu Lys Val Ala Gly Phe
                245                 250                 255

Asn Leu Leu Met Thr Leu Arg Leu Trp Ser Ser
                260                 265
```

<210> SEQ ID NO 5
<211> LENGTH: 804
<212> TYPE: DNA
<213> ORGANISM: Artificial Sequence
<220> FEATURE:
<223> OTHER INFORMATION: TRA specific for E5 epitope, optimized

<400> SEQUENCE: 5

```
atggaaacac tgctgggcgt gtccctcgtg atcctgtggc tgcagctggc tagagtgaac        60
agccagcagg gcgaggaaga tcctcaggcc ctgagcatcc aggaaggcga gaacgccacc       120
atgaactgca gctacaagac cagcatcaac aacctgcagt ggtacaggca gaatagcggc       180
agaggactgg tgcacctgat cctgatccgg tccaacgaga gagaagca ctccggcaga         240 ctgagagtga ccctggacac ctccaagaag tccagctccc tgctgattac cgccagcaga       300
gccgccgata ccgcctccta cttttgcgcc gagagcgagt acggcaacaa gctggtgttt       360
ggcgccggaa ccatcctgcg cgtgaagtcc tacatccaga accccgagcc cgccgtgtat       420
cagctgaagg accccagaag ccaggacagc accctgtgcc tgttcaccga cttcgacagc       480
cagatcaacg tgcccaagac catggaaagc ggcaccttca tcaccgataa gaccgtgctg       540
gacatgaagg ccatggacag caagagcaac ggcgccattg cctggtccaa ccagaccagc       600
ttcacatgcc aggacatctt caaagagaca acgccacct accccagcag cgacgtgccc        660
tgtgatgcca ccctgaccga agtccttc gagacagaca tgaatctgaa cttccagaac         720
ctgagcgtga tgggcctgag aatcctgctg ctgaaggtgg ccggcttcaa cctgctgatg       780
accctgagac tgtggtccag ctga                                              804
```

<210> SEQ ID NO 6
<211> LENGTH: 13
<212> TYPE: PRT
<213> ORGANISM: Artificial Sequence
<220> FEATURE:
<223> OTHER INFORMATION: CDR3 of TRB specific for E5 epitope

<400> SEQUENCE: 6

Cys Ala Ser Ser Tyr Arg Gln Gln Glu Thr Gln Tyr Phe
1               5                   10

<210> SEQ ID NO 7
<211> LENGTH: 131
<212> TYPE: PRT
<213> ORGANISM: Artificial Sequence
<220> FEATURE:
<223> OTHER INFORMATION: variable region of TRB specific for E5 epitope,
      TRBV6-5

<400> SEQUENCE: 7

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

```
Leu Leu Ser Ala Ala Pro Ser Gln Thr Ser Val Tyr Phe Cys Ala Ser
            100                 105                 110

Ser Tyr Arg Gln Gln Glu Thr Gln Tyr Phe Gly Pro Gly Thr Arg Leu
        115                 120                 125

Leu Val Leu
    130

<210> SEQ ID NO 8
<211> LENGTH: 304
<212> TYPE: PRT
<213> ORGANISM: Artificial Sequence
<220> FEATURE:
<223> OTHER INFORMATION: TRB specific for E5 epitope, optimized

<400> SEQUENCE: 8

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Arg Gln Gln Glu Thr Gln Tyr Phe Gly Pro Gly Thr Arg Leu
        115                 120                 125

Leu Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr His Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Gly Leu Val Leu Met Ala Met Val Lys Lys Lys Asn Ser
    290                 295                 300

<210> SEQ ID NO 9
```

<211> LENGTH: 915
<212> TYPE: DNA
<213> ORGANISM: Artificial Sequence
<220> FEATURE:
<223> OTHER INFORMATION: TRB specific for E5 epitope, optimized

<400> SEQUENCE: 9

```
atgtctatcg gcctgctgtg ttgtgccgcc ctgtccctgc tgtgggccgg acctgtgaat    60
gctggcgtga cccagacccc caagttccag gtgctgaaaa ccggccagag catgaccctg   120
cagtgcgccc aggacatgaa ccacgagtac atgagctggt acagacagga ccccggcatg   180
ggcctgcggc tgatccacta ttctgtggga gccggcatca ccgaccaggg cgaagtgccc   240
aatggctaca acgtgtccag aagcaccacc gaggacttcc cactgcggct gctgtctgcc   300
gccccatctc agaccagcgt gtacttctgc gccagcagct accggcagca ggaaacccag   360
tacttcggcc ctggcaccag actgctggtg ctggaagatc tgcggaacgt gacccccccc   420
aaggtgtccc tgttcgagcc tagcaaggcc gagatcgcca acaagcagaa agccacccttc   480
gtgtgcctgg ccagaggctt cttccccgac catgtggaac tgtcttggtg ggtcaacggc   540
aaagaggtgc acagcggcgt gtccaccgat ccccaggcct acaaagagag caactacagc   600
tactgcctga gcagcaggct gcgggtgtcc gccaccttct ggcacaaccc ccggaaccac   660
ttcagatgcc aggtgcagtt ccacggcctg agcgaagagg acaagtggcc tgagggcagc   720
cccaagcccg tgcacagaa tatctctgcc gaagcctggg gcagagccga ctgtggcatt   780
accagcgcca gctaccatca gggcgtgctg agcgccacca tcctgtacga gatcctgctg   840
ggcaaggcca ccctgtacgc cgtgctggtg tcaggcctgg tgctgatggc catggtcaag   900
aagaagaaca gctga                                                    915
```

<210> SEQ ID NO 10
<211> LENGTH: 10
<212> TYPE: PRT
<213> ORGANISM: Cytomegalovirus
<220> FEATURE:
<223> OTHER INFORMATION: CMV pp65 epitope restricted to HLA-B*07:02

<400> SEQUENCE: 10

Thr Pro Arg Val Thr Gly Gly Gly Ala Met
1               5                   10

<210> SEQ ID NO 11
<211> LENGTH: 15
<212> TYPE: PRT
<213> ORGANISM: Artificial Sequence
<220> FEATURE:
<223> OTHER INFORMATION: CDR3 of TRA specific for pp65 epitope

<400> SEQUENCE: 11

Cys Ala Thr Val Ile Arg Met Asp Ser Ser Tyr Lys Leu Ile Phe
1               5                   10                  15

<210> SEQ ID NO 12
<211> LENGTH: 134
<212> TYPE: PRT
<213> ORGANISM: Artificial Sequence
<220> FEATURE:
<223> OTHER INFORMATION: variable region of TRA specific for pp65
      epitope, TRAV17

<400> SEQUENCE: 12

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Val
            100                 105                 110

Ile Arg Met Asp Ser Ser Tyr Lys Leu Ile Phe Gly Ser Gly Thr Arg
        115                 120                 125

Leu Leu Val Arg Pro Asp
        130

<210> SEQ ID NO 13
<211> LENGTH: 270
<212> TYPE: PRT
<213> ORGANISM: Artificial Sequence
<220> FEATURE:
<223> OTHER INFORMATION: TRA specific for pp65 epitope, optimized

<400> SEQUENCE: 13

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Val
            100                 105                 110

Ile Arg Met Asp Ser Ser Tyr Lys Leu Ile Phe Gly Ser Gly Thr Arg
        115                 120                 125

Leu Leu Val Arg Pro Asp Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Lys Val
                245                 250                 255

Ala Gly Phe Asn Leu Leu Met Thr Leu Arg Leu Trp Ser Ser
            260                 265                 270

<210> SEQ ID NO 14
<211> LENGTH: 813
<212> TYPE: DNA
<213> ORGANISM: Artificial Sequence
<220> FEATURE:
<223> OTHER INFORMATION: TRA specific for pp65 epitope, optimized

<400> SEQUENCE: 14
atggaaacac tgctgggcgt gtcactcgtg atcctgtggc tgcagctggc tagagtgaac      60
agccagcagg gggaagagga ccctcaggcc ctgagcattc aggaaggcga aacgccacc     120 atgaactgca gctacaagac cagcatcaac aacctgcagt ggtacaggca gaactccggc     180
agaggactgg tgcacctgat cctgatccgg tccaacgaga gagaagcca ctccggacgg     240 ctgagagtga ccctggacac ctccaagaag tccagctccc tgctgattac cgccagcaga     300
gccgccgata ccgcctccta cttttgcgcc accgtgatcc ggatggacag ctcctacaag     360
ctgatctttg gcagcggcac cagactgctc gtgcggcccg atatccagaa ccctgagcct     420
gccgtgtacc agctgaagga ccccagaagc caggacagca cactgtgcct gttcaccgac     480
ttcgacagcc agatcaacgt gcccaagacc atggaaagcg gcaccttcat caccgacaag     540
acagtgctgg acatgaaggc catggacagc aagagcaacg cgccattgc ctggtccaac     600 cagaccagct tcacatgcca ggacatcttc aaagagacaa cgccaccta ccccagcagc     660 gacgtgccct gtgatgccac cctgaccgag aagtccttcg agacagacat gaacctgaat     720
ttccagaacc tgtccgtgat gggcctgaga atcctgctgc tgaaggtggc cggcttcaat     780
ctgctgatga ccctgcggct gtggtccagc tga                                 813

<210> SEQ ID NO 15
<211> LENGTH: 16
<212> TYPE: PRT
<213> ORGANISM: Artificial Sequence
<220> FEATURE:
<223> OTHER INFORMATION: CDR3 of TRB specific for pp65 epitope

<400> SEQUENCE: 15

Cys Ala Ser Ser Leu Ile Gly Val Ser Ser Tyr Asn Glu Gln Phe Phe
1               5                   10                  15

<210> SEQ ID NO 16
<211> LENGTH: 135
<212> TYPE: PRT
<213> ORGANISM: Artificial Sequence
<220> FEATURE:
<223> OTHER INFORMATION: variable region of TRB specific for pp65
      epitope, TRBV7-9

<400> SEQUENCE: 16

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
                100                 105                 110

Ser Ser Leu Ile Gly Val Ser Ser Tyr Asn Glu Gln Phe Phe Gly Pro
            115                 120                 125

Gly Thr Arg Leu Thr Val Leu
        130             135

<210> SEQ ID NO 17
<211> LENGTH: 308
<212> TYPE: PRT
<213> ORGANISM: Artificial Sequence
<220> FEATURE:
<223> OTHER INFORMATION: TRB specific for pp65 epitope, optimized

<400> SEQUENCE: 17

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
                20                  25                  30

Lys Arg Gly Gln Asn Val Thr Phe Arg Cys Asp Pro Ile Ser Glu His
            35                  40                  45

Asn Arg Leu Tyr Trp Tyr Arg Gln Thr Leu Gly Gln Gly Pro Glu Phe
        50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
                100                 105                 110

Ser Ser Leu Ile Gly Val Ser Ser Tyr Asn Glu Gln Phe Phe Gly Pro
            115                 120                 125

Gly Thr Arg Leu Thr Val Leu Glu Asp Leu Arg Asn Val Thr Pro Pro
        130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Ser
                180                 185                 190

Thr Asp Pro Gln Ala Tyr Lys Glu Ser Asn Tyr Ser Tyr Cys Leu Ser
            195                 200                 205

Ser Arg Leu Arg Val Ser Ala Thr Phe Trp His Asn Pro Arg Asn His
        210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr His Gln Gly
                260                 265                 270

Val Leu Ser Ala Thr Ile Leu Tyr Glu Ile Leu Leu Gly Lys Ala Thr

```
                275                 280                 285
Leu Tyr Ala Val Leu Val Ser Gly Leu Val Leu Met Ala Met Val Lys
        290                 295                 300

Lys Lys Asn Ser
305
```

<210> SEQ ID NO 18
<211> LENGTH: 927
<212> TYPE: DNA
<213> ORGANISM: Artificial Sequence
<220> FEATURE:
<223> OTHER INFORMATION: TRB specific for pp65 epitope, optimized

<400> SEQUENCE: 18

```
atgggaacat ctctgctgtg ttggatggcc ctgtgcctgc tgggagccga tcatgccgat      60
acaggcgtgt cccaggaccc ccggcacaag attaccaagc ggggccagaa cgtgaccttc     120
agatgcgacc ccatcagcga gcacaaccgg ctgtactggt acagacagac cctgggccag     180
ggaccccagt tcctgaccta cttccagaac gaggcccagc tggaaaagag ccggctgctg     240
agcgacagat tcagcgccga aagacccaag ggcagcttca gcaccctgga aatccagcgg     300
accgagcagg gcgacagcgc catgtatctg tgtgccagca gctgatcgg cgtgtccagc     360
tacaacgagc agttcttcgg ccctggcacc cggctgaccg tgctggaaga tctgagaaac     420
gtgaccccc ccaaggtgtc cctgttcgag cctagcaagg ccgagatcgc caacaagcag     480
aaagccaccc tcgtgtgcct ggccagaggc ttcttccccg accatgtgga actgtcttgg     540
tgggtcaacg gcaaagaggt gcacagcgga gtgtccaccg accccaggc ctacaaagag     600
agcaactaca gctactgcct gagcagcaga ctgcgggtgt ccgccacctt ctggcacaac     660
ccccggaacc acttcaggtg ccaggtgcag tttcacggcc tgagcgaaga ggacaagtgg     720
cccgagggca gccctaagcc cgtgacccag aatatctctg ccgaagcctg ggcagagcc     780
gactgtggca ttaccagcgc cagctaccat cagggcgtgc tgagcgccac catcctgtac     840
gagatcctgc tgggcaaggc cacctgtac gccgtgctgg tgtctggcct ggtgctgatg     900
gccatggtca agaagaagaa cagctga                                         927
```

<210> SEQ ID NO 19
<211> LENGTH: 14
<212> TYPE: PRT
<213> ORGANISM: Artificial Sequence
<220> FEATURE:
<223> OTHER INFORMATION: Homsap TRAV38-2/DV8*01 F

<400> SEQUENCE: 19

```
Cys Ala Tyr Arg Ser Trp Asn Tyr Gly Gln Asn Phe Val Phe
1               5                   10
```

<210> SEQ ID NO 20
<211> LENGTH: 14
<212> TYPE: PRT
<213> ORGANISM: Artificial Sequence
<220> FEATURE:
<223> OTHER INFORMATION: Homsap TRAV8-6*02 F

<400> SEQUENCE: 20

```
Cys Ala Val Ser Glu Pro Ala Ala Gly Asn Lys Leu Thr Phe
1               5                   10
```

<210> SEQ ID NO 21
<211> LENGTH: 16

```
<212> TYPE: PRT
<213> ORGANISM: Artificial Sequence
<220> FEATURE:
<223> OTHER INFORMATION: Homsap TRAV26-2*01 F

<400> SEQUENCE: 21

Cys Ile Leu Arg Gly Ala Gly Gly Thr Ser Tyr Gly Lys Leu Thr Phe
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: Homsap TRAV8-6*02 F

<400> SEQUENCE: 22

Cys Ala Val Ile Thr Asn Ala Gly Lys Ser Thr Phe
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Homsap TRAV25*01 F

<400> SEQUENCE: 23

Cys Ala Gly Pro Pro Ser Gly Thr Tyr Lys Tyr Ile Phe
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Homsap TRAV6*02 (F)

<400> SEQUENCE: 24

Cys Ala Leu Pro Met Glu Tyr Gly Asn Lys Leu Val Phe
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Homsap TRBV5-1*01 F

<400> SEQUENCE: 25

Cys Ala Ser Ser Ser Arg Gly His Gln Asn Thr Gly Glu Leu Phe Phe
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Homsap TRBV12-3*01 F

<400> SEQUENCE: 26

Cys Ala Ser Ser Pro Glu Gly Glu Gly Val Thr Gly Glu Leu Phe Phe
1               5                   10                  15

<210> SEQ ID NO 27
<211> LENGTH: 13
<212> TYPE: PRT
```

```
<213> ORGANISM: Artificial Sequence
<220> FEATURE:
<223> OTHER INFORMATION: Homsap TRBV5-1*01 F

<400> SEQUENCE: 27

Cys Ala Ser Thr Leu Arg Gly Tyr Thr Glu Ala Phe Phe
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Homsap TRBV5-5*02 (F)

<400> SEQUENCE: 28

Cys Ala Ser Ser Pro Trp Ala Asp Ser Asn Gln Pro Gln His Phe
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Homsap TRBV20-1*01 F

<400> SEQUENCE: 29

Cys Ser Ala Gly Thr Ser Gly Gly Pro Ala Tyr Glu Gln Tyr Phe
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Homsap TRBV27*01 F

<400> SEQUENCE: 30

Cys Ala Ser Ser Ser Pro Leu Ala Asp Asp Tyr Asn Glu Gln Phe Phe
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Homsap TRBV6-2*01 F

<400> SEQUENCE: 31

Cys Ala Ser Ser His Arg Arg Ala His Arg Ala Arg Glu Gln Tyr Phe
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Homsap TRAV14/DV4*01 F

<400> SEQUENCE: 32

Cys Ala Met Arg Glu Gly Lys Asp Ser Ser Tyr Lys Leu Ile Phe
1               5                   10                  15

<210> SEQ ID NO 33
<211> LENGTH: 14
<212> TYPE: PRT
<213> ORGANISM: Artificial Sequence
```

```
<220> FEATURE:
<223> OTHER INFORMATION: Homsap TRAV8-1*01 F

<400> SEQUENCE: 33

Cys Ala Val Asn Arg Gly Gly Ser Asn Tyr Lys Leu Thr Phe
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Homsap TRAV3*01 F

<400> SEQUENCE: 34

Cys Ala Val Arg Asp Ile Gly Gly Phe Lys Thr Ile Phe
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Homsap TRAV1-2*01 F

<400> SEQUENCE: 35

Cys Ala Leu Asp Gly Gln Lys Leu Leu Phe
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Homsap TRAV4*01 F

<400> SEQUENCE: 36

Cys Leu Val Gly Gly Leu Arg Gly Asn Val Leu His Cys
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Homsap TRBV27*01 F

<400> SEQUENCE: 37

Cys Ala Ser Arg Leu Gly Gly Gly Asn Tyr Asn Glu Gln Phe Phe
1               5                   10                  15

<210> SEQ ID NO 38
<211> LENGTH: 17
<212> TYPE: PRT
<213> ORGANISM: Artificial Sequence
<220> FEATURE:
<223> OTHER INFORMATION: Homsap TRBV20-1*01 F

<400> SEQUENCE: 38

Cys Ser Ala Ser Pro Arg Asp Arg Lys Phe Ser Gly Asn Thr Ile Tyr
1               5                   10                  15

Phe

<210> SEQ ID NO 39
<211> LENGTH: 17
<212> TYPE: PRT
```

<213> ORGANISM: Artificial Sequence
<220> FEATURE:
<223> OTHER INFORMATION: Homsap TRBV7-9*03 F

<400> SEQUENCE: 39

Cys Ala Ser Ser His Asp Asn Gln Gly Ala Lys Ser Pro Leu His
1               5                   10                  15

Phe

<210> SEQ ID NO 40
<211> LENGTH: 1782
<212> TYPE: DNA
<213> ORGANISM: Artificial Sequence
<220> FEATURE:
<223> OTHER INFORMATION: TCR transgene cassette specific for the E5
      epitope

<400> SEQUENCE: 40

```
atgtctatcg gcctgctgtg ttgtgccgcc ctgtccctgc tgtgggccgg acctgtgaat     60
gctggcgtga cccagacccc caagttccag gtgctgaaaa ccggccagag catgaccctg    120
cagtgcgccc aggacatgaa ccacgagtac atgagctggt acagacagga ccccggcatg    180
ggcctgcggc tgatccacta ttctgtggga gccggcatca ccgaccaggg cgaagtgccc    240
aatggctaca cgtgtccag aagcaccacc gaggacttcc cactgcggct gctgtctgcc    300
gccccatctc agaccagcgt gtacttctgc gccagcagct accggcagca ggaaacccag    360
tacttcggcc tggcaccag actgctggtg ctggaagatc tgcggaacgt gacccccccc    420
aaggtgtccc tgttcgagcc tagcaaggcc gagatcgcca acaagcagaa gccacccctc    480
gtgtgcctgg ccagaggctt cttccccgac catgtggaac tgtcttggtg ggtcaacggc    540
aaagaggtgc acagcggcgt gtccaccgat ccccaggcct acaaagagag caactacagc    600
tactgcctga gcagcaggct gcgggtgtcc gccaccttct ggcacaaccc ccggaaccac    660
ttcagatgcc aggtgcagtt ccacggcctg agcgaagagg acaagtggcc tgagggcagc    720
cccaagcccg tgacacagaa tatctctgcc gaagcctggg gcagagccga ctgtggcatt    780
accagcgcca gctaccatca gggcgtgctg agcgccacca tcctgtacga gatcctgctg    840
ggcaaggcca ccctgtacgc cgtgctggtg tcaggcctgg tgctgatggc catggtcaag    900
aagaagaaca cgcggcagcg gcgccaccaa ctttagcctgc tgaaacaggc cggcgacgtg    960
gaagagaacc ccgggcccat ggaaacactg ctgggcgtgt ccctcgtgat cctgtggctg   1020
cagctggcta gagtgaacag ccagcagggc gaggaagatc ctcaggccct gagcatccag   1080
gaaggcgaga acgccaccat gaactgcagc tacaagacca gcatcaacaa cctgcagtgg   1140
tacaggcaga taccggcag aggactggtg cacctgatcc tgatccggtc caacgagaga   1200
gagaagcact ccggcagact gagagtgacc ctggacacct ccaagaagtc cagctccctg   1260
ctgattaccg ccagcagagc cgccgatacc gcctcctact tttgcgccga gagcgagtac   1320
ggcaacaagc tggtgtttgg cgccggaacc atcctgcgcg tgaagtccta catccagaac   1380
cccgagcccg ccgtgtatca gctgaaggac cccagaagcc aggacagcac cctgtgcctg   1440
ttcaccgact cgacagcca gatcaacgtg cccaagacca tggaaagcgg caccttcatc   1500
accgataaga ccgtgctgga catgaaggcc atggacagca gagcaacgg cgccattgcc   1560
tggtccaacc agaccagctt cacatgccag gacatcttca agagacaaa cgccacctac   1620
cccagcagcg acgtgccctg tgatgccacc ctgaccgaga gtccttcga cagacatg   1680
aatctgaact tccagaacct gagcgtgatg ggcctgagaa tcctgctgct gaaggtggcc   1740
```

```
ggcttcaacc tgctgatgac cctgagactg tggtccagct ga              1782
```

<210> SEQ ID NO 41
<211> LENGTH: 1803
<212> TYPE: DNA
<213> ORGANISM: Artificial Sequence
<220> FEATURE:
<223> OTHER INFORMATION: TCR transgene cassette specific for the pp65
      epitope

<400> SEQUENCE: 41

```
atgggaacat ctctgctgtg ttggatggcc ctgtgcctgc tgggagccga tcatgccgat     60
acaggcgtgt cccaggaccc ccggcacaag attaccaagc ggggccagaa cgtgaccttc    120
agatgcgacc ccatcagcga gcacaaccgg ctgtactggt acagacagac cctgggccag    180
ggacccgagt tcctgaccta cttccagaac gaggcccagc tggaaaagag ccggctgctg    240
agcgacagat tcagcgccga aagacccaag ggcagcttca gcaccctgga aatccagcgg    300
accgagcagg gcgacagcgc catgtatctg tgtgccagca gcctgatcgg cgtgtccagc    360
tacaacgagc agttcttcgg ccctggcacc cggctgaccg tgctggaaga tctgagaaac    420
gtgaccccc ccaaggtgtc cctgttcgag cctagcaagg ccgagatcgc caacaagcag    480
aaagccaccc tcgtgtgcct ggccagaggc ttcttccccg accatgtgga actgtcttgg    540
tgggtcaacg gcaaagaggt gcacagcgga gtgtccaccg accccaggc ctacaaagag    600
agcaactaca gctactgcct gagcagcaga ctgcgggtgt ccgccacctt ctggcacaac    660
ccccggaacc acttcaggtg ccaggtgcag tttcacggcc tgagcgaaga ggacaagtgg    720
cccgagggca gccctaagcc cgtgacccag aatatctctg ccgaagcctg ggcagagcc    780
gactgtggca ttaccagcgc cagctaccat caggcgtgc tgagcgccac catcctgtac    840
gagatcctgc tgggcaaggc caccctgtac gccgtgctgg tgtctggcct ggtgctgatg    900
gccatggtca agaagaagaa cagcggcagc ggcgccacca acttcagcct gctgaaacag    960
gccggcgacg tggaagagaa ccccgggccc atggaaacac tgctgggcgt gtcactcgtg   1020
atcctgtggc tgcagctggc tagagtgaac agccagcagg gggaagagga ccctcaggcc   1080
ctgagcattc aggaaggcga gaacgccacc atgaactgca gctacaagac cagcatcaac   1140
aacctgcagt ggtacaggca gaactccggc agaggactgg tgcacctgat cctgatccgg   1200
tccaacgaga gagagaagca ctccggacgg ctgagagtga ccctggacac ctccaagaag   1260
tccagctccc tgctgattac cgccagcaga gccgccgata ccgcctccta cttttgcgcc   1320
accgtgatcc ggatggacag ctcctacaag ctgatctttg gcagcggcac cagactgctc   1380
gtgcggcccg atatccagaa ccctgagcct gccgtgtacc agctgaagga ccccagaagc   1440
caggacagca cactgtgcct gttcaccgac ttcgacagcc agatcaacgt gcccaagacc   1500
atggaaagcg gcaccttcat caccgacaag acagtgctgg acatgaaggc catggacagc   1560
aagagcaacg gcgccattgc ctggtccaac cagaccagct tcacatgcca ggacatcttc   1620
aaagagacaa acgccaccta ccccagcagc gacgtgccct gtgatgccac cctgaccgag   1680
aagtccttcg agacagacat gaacctgaat ttccagaacc tgtccgtgat gggcctgaga   1740
atcctgctgc tgaaggtggc cggcttcaat ctgctgatga ccctgcggct gtggtccagc   1800
tga                                                                 1803
```

<210> SEQ ID NO 42
<211> LENGTH: 12

```
<212> TYPE: PRT
<213> ORGANISM: Alphapapillomavirus 9
<220> FEATURE:
<223> OTHER INFORMATION: potential epitope of E5

<400> SEQUENCE: 42

Leu Ile Arg Pro Leu Leu Leu Ser Val Ser Thr Tyr
1               5                   10

<210> SEQ ID NO 43
<211> LENGTH: 13
<212> TYPE: PRT
<213> ORGANISM: Alphapapillomavirus 9
<220> FEATURE:
<223> OTHER INFORMATION: potential epitope of E5

<400> SEQUENCE: 43

Leu Leu Ile Arg Pro Leu Leu Leu Ser Val Ser Thr Tyr
1               5                   10

<210> SEQ ID NO 44
<211> LENGTH: 9
<212> TYPE: PRT
<213> ORGANISM: Alphapapillomavirus 9
<220> FEATURE:
<223> OTHER INFORMATION: potential epitope of E5

<400> SEQUENCE: 44

Phe Leu Ile His Thr His Ala Arg Phe
1               5

<210> SEQ ID NO 45
<211> LENGTH: 10
<212> TYPE: PRT
<213> ORGANISM: Alphapapillomavirus 9
<220> FEATURE:
<223> OTHER INFORMATION: potential epitope of E5

<400> SEQUENCE: 45

Ala Ser Ala Phe Arg Cys Phe Ile Val Tyr
1               5                   10

<210> SEQ ID NO 46
<211> LENGTH: 10
<212> TYPE: PRT
<213> ORGANISM: Alphapapillomavirus 9
<220> FEATURE:
<223> OTHER INFORMATION: potential epitope of E5

<400> SEQUENCE: 46

Leu Leu Trp Ile Thr Ala Ala Ser Ala Phe
1               5                   10

<210> SEQ ID NO 47
<211> LENGTH: 13
<212> TYPE: PRT
<213> ORGANISM: Alphapapillomavirus 9
<220> FEATURE:
<223> OTHER INFORMATION: epitope of E5

<400> SEQUENCE: 47

Ile Thr Ala Ala Ser Ala Phe Arg Cys Phe Ile Val Tyr
1               5                   10

<210> SEQ ID NO 48
<211> LENGTH: 8
<212> TYPE: PRT
```

<213> ORGANISM: Alphapapillomavirus 9
<220> FEATURE:
<223> OTHER INFORMATION: potential epitope of E5

<400> SEQUENCE: 48

Leu Leu Leu Ser Val Ser Thr Tyr
1               5

<210> SEQ ID NO 49
<211> LENGTH: 11
<212> TYPE: PRT
<213> ORGANISM: Alphapapillomavirus 9
<220> FEATURE:
<223> OTHER INFORMATION: epitope of E5

<400> SEQUENCE: 49

Ala Ala Ser Ala Phe Arg Cys Phe Ile Val Tyr
1               5                   10

<210> SEQ ID NO 50
<211> LENGTH: 14
<212> TYPE: PRT
<213> ORGANISM: Alphapapillomavirus 9
<220> FEATURE:
<223> OTHER INFORMATION: potential epitope of E5

<400> SEQUENCE: 50

Ser Ala Phe Arg Cys Phe Ile Val Tyr Ile Ile Phe Val Tyr
1               5                   10

<210> SEQ ID NO 51
<211> LENGTH: 14
<212> TYPE: PRT
<213> ORGANISM: Alphapapillomavirus 9
<220> FEATURE:
<223> OTHER INFORMATION: epitope of E5

<400> SEQUENCE: 51

Trp Ile Thr Ala Ala Ser Ala Phe Arg Cys Phe Ile Val Tyr
1               5                   10

<210> SEQ ID NO 52
<211> LENGTH: 12
<212> TYPE: PRT
<213> ORGANISM: Alphapapillomavirus 9
<220> FEATURE:
<223> OTHER INFORMATION: epitope of E5

<400> SEQUENCE: 52

Thr Ala Ala Ser Ala Phe Arg Cys Phe Ile Val Tyr
1               5                   10

<210> SEQ ID NO 53
<211> LENGTH: 11
<212> TYPE: PRT
<213> ORGANISM: Alphapapillomavirus 9
<220> FEATURE:
<223> OTHER INFORMATION: potential epitope of E5

<400> SEQUENCE: 53

Leu Leu Leu Trp Ile Thr Ala Ala Ser Ala Phe
1               5                   10

<210> SEQ ID NO 54
<211> LENGTH: 9
<212> TYPE: PRT
<213> ORGANISM: Alphapapillomavirus 9

<220> FEATURE:
<223> OTHER INFORMATION: potential epitope of E5

<400> SEQUENCE: 54

Leu Leu Ala Cys Phe Leu Leu Cys Phe
1               5

<210> SEQ ID NO 55
<211> LENGTH: 8
<212> TYPE: PRT
<213> ORGANISM: Alphapapillomavirus 9
<220> FEATURE:
<223> OTHER INFORMATION: potential epitope of E5

<400> SEQUENCE: 55

Trp Ile Thr Ala Ala Ser Ala Phe
1               5

<210> SEQ ID NO 56
<211> LENGTH: 8
<212> TYPE: PRT
<213> ORGANISM: Alphapapillomavirus 9
<220> FEATURE:
<223> OTHER INFORMATION: potential epitope of E5

<400> SEQUENCE: 56

Leu Ile His Thr His Ala Arg Phe
1               5

<210> SEQ ID NO 57
<211> LENGTH: 13
<212> TYPE: PRT
<213> ORGANISM: Alphapapillomavirus 9
<220> FEATURE:
<223> OTHER INFORMATION: epitope of E5

<400> SEQUENCE: 57

Leu Leu Trp Ile Thr Ala Ala Ser Ala Phe Arg Cys Phe
1               5                   10

<210> SEQ ID NO 58
<211> LENGTH: 593
<212> TYPE: PRT
<213> ORGANISM: Artificial Sequence
<220> FEATURE:
<223> OTHER INFORMATION: TCR cassette specific for the E5 epitope

<400> SEQUENCE: 58

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Arg Gln Gln Glu Thr Gln Tyr Phe Gly Pro Gly Thr Arg Leu

-continued

```
            115                 120                 125
Leu Val Leu Glu Asp Leu Arg Asn Val Thr Pro Pro Lys Val Ser Leu
            130                 135                 140
Phe Glu Pro Ser Lys Ala Glu Ile Ala Asn Lys Gln Lys Ala Thr Leu
145                 150                 155                 160
Val Cys Leu Ala Arg Gly Phe Phe Pro Asp His Val Glu Leu Ser Trp
                    165                 170                 175
Trp Val Asn Gly Lys Glu Val His Ser Gly Val Ser Thr Asp Pro Gln
                    180                 185                 190
Ala Tyr Lys Glu Ser Asn Tyr Ser Tyr Cys Leu Ser Ser Arg Leu Arg
                    195                 200                 205
Val Ser Ala Thr Phe Trp His Asn Pro Arg Asn His Phe Arg Cys Gln
            210                 215                 220
Val Gln Phe His Gly Leu Ser Glu Glu Asp Lys Trp Pro Glu Gly Ser
225                 230                 235                 240
Pro Lys Pro Val Thr Gln Asn Ile Ser Ala Glu Ala Trp Gly Arg Ala
                    245                 250                 255
Asp Cys Gly Ile Thr Ser Ala Ser Tyr His Gln Gly Val Leu Ser Ala
                    260                 265                 270
Thr Ile Leu Tyr Glu Ile Leu Leu Gly Lys Ala Thr Leu Tyr Ala Val
                    275                 280                 285
Leu Val Ser Gly Leu Val Leu Met Ala Met Val Lys Lys Lys Asn Ser
            290                 295                 300
Gly Ser Gly Ala Thr Asn Phe Ser Leu Leu Lys Gln Ala Gly Asp Val
305                 310                 315                 320
Glu Glu Asn Pro Gly Pro Met Glu Thr Leu Leu Gly Val Ser Leu Val
                    325                 330                 335
Ile Leu Trp Leu Gln Leu Ala Arg Val Asn Ser Gln Gln Gly Glu Glu
                    340                 345                 350
Asp Pro Gln Ala Leu Ser Ile Gln Glu Gly Glu Asn Ala Thr Met Asn
                    355                 360                 365
Cys Ser Tyr Lys Thr Ser Ile Asn Asn Leu Gln Trp Tyr Arg Gln Asn
            370                 375                 380
Ser Gly Arg Gly Leu Val His Leu Ile Leu Ile Arg Ser Asn Glu Arg
385                 390                 395                 400
Glu Lys His Ser Gly Arg Leu Arg Val Thr Leu Asp Thr Ser Lys Lys
                    405                 410                 415
Ser Ser Ser Leu Leu Ile Thr Ala Ser Arg Ala Ala Asp Thr Ala Ser
                    420                 425                 430
Tyr Phe Cys Ala Glu Ser Glu Tyr Gly Asn Lys Leu Val Phe Gly Ala
                    435                 440                 445
Gly Thr Ile Leu Arg Val Lys Ser Tyr Ile Gln Asn Pro Glu Pro Ala
            450                 455                 460
Val Tyr Gln Leu Lys Asp Pro Arg Ser Gln Asp Ser Thr Leu Cys Leu
465                 470                 475                 480
Phe Thr Asp Phe Asp Ser Gln Ile Asn Val Pro Lys Thr Met Glu Ser
                    485                 490                 495
Gly Thr Phe Ile Thr Asp Lys Thr Val Leu Asp Met Lys Ala Met Asp
                    500                 505                 510
Ser Lys Ser Asn Gly Ala Ile Ala Trp Ser Asn Gln Thr Ser Phe Thr
            515                 520                 525
Cys Gln Asp Ile Phe Lys Glu Thr Asn Ala Thr Tyr Pro Ser Ser Asp
            530                 535                 540
```

-continued

Val Pro Cys Asp Ala Thr Leu Thr Glu Lys Ser Phe Glu Thr Asp Met
545                 550                 555                 560

Asn Leu Asn Phe Gln Asn Leu Ser Val Met Gly Leu Arg Ile Leu Leu
            565                 570                 575

Leu Lys Val Ala Gly Phe Asn Leu Leu Met Thr Leu Arg Leu Trp Ser
        580                 585                 590

Ser

<210> SEQ ID NO 59
<211> LENGTH: 600
<212> TYPE: PRT
<213> ORGANISM: Artificial Sequence
<220> FEATURE:
<223> OTHER INFORMATION: TCR cassette specific for the pp65 epitope

<400> SEQUENCE: 59

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Ile Gly Val Ser Ser Tyr Asn Glu Gln Phe Phe Gly Pro
        115                 120                 125

Gly Thr Arg Leu Thr Val Leu Glu Asp Leu Arg Asn Val Thr Pro Pro
130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr His Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Gly Leu Val Leu Met Ala Met Val Lys
290                 295                 300

-continued

| | | | | | | | | | | | | |
|---|---|---|---|---|---|---|---|---|---|---|---|---|
| Lys | Lys | Asn | Ser | Gly | Ser | Gly | Ala | Thr | Asn | Phe | Ser | Leu | Leu | Lys | Gln |
| 305 | | | | 310 | | | | | 315 | | | | | 320 | |

Lys Lys Asn Ser Gly Ser Gly Ala Thr Asn Phe Ser Leu Leu Lys Gln
305                 310                 315                 320

Ala Gly Asp Val Glu Glu Asn Pro Gly Pro Met Glu Thr Leu Leu Gly
                325                 330                 335

Val Ser Leu Val Ile Leu Trp Leu Gln Leu Ala Arg Val Asn Ser Gln
                340                 345                 350

Gln Gly Glu Glu Asp Pro Gln Ala Leu Ser Ile Gln Glu Gly Glu Asn
                355                 360                 365

Ala Thr Met Asn Cys Ser Tyr Lys Thr Ser Ile Asn Asn Leu Gln Trp
370                 375                 380

Tyr Arg Gln Asn Ser Gly Arg Gly Leu Val His Leu Ile Leu Ile Arg
385                 390                 395                 400

Ser Asn Glu Arg Glu Lys His Ser Gly Arg Leu Arg Val Thr Leu Asp
                405                 410                 415

Thr Ser Lys Lys Ser Ser Ser Leu Leu Ile Thr Ala Ser Arg Ala Ala
                420                 425                 430

Asp Thr Ala Ser Tyr Phe Cys Ala Thr Val Ile Arg Met Asp Ser Ser
                435                 440                 445

Tyr Lys Leu Ile Phe Gly Ser Gly Thr Arg Leu Leu Val Arg Pro Asp
450                 455                 460

Ile Gln Asn Pro Glu Pro Ala Val Tyr Gln Leu Lys Asp Pro Arg Ser
465                 470                 475                 480

Gln Asp Ser Thr Leu Cys Leu Phe Thr Asp Phe Asp Ser Gln Ile Asn
                485                 490                 495

Val Pro Lys Thr Met Glu Ser Gly Thr Phe Ile Thr Asp Lys Thr Val
                500                 505                 510

Leu Asp Met Lys Ala Met Asp Ser Lys Ser Asn Gly Ala Ile Ala Trp
                515                 520                 525

Ser Asn Gln Thr Ser Phe Thr Cys Gln Asp Ile Phe Lys Glu Thr Asn
530                 535                 540

Ala Thr Tyr Pro Ser Ser Asp Val Pro Cys Asp Ala Thr Leu Thr Glu
545                 550                 555                 560

Lys Ser Phe Glu Thr Asp Met Asn Leu Asn Phe Gln Asn Leu Ser Val
                565                 570                 575

Met Gly Leu Arg Ile Leu Leu Leu Lys Val Ala Gly Phe Asn Leu Leu
                580                 585                 590

Met Thr Leu Arg Leu Trp Ser Ser
                595                 600

<210> SEQ ID NO 60
<211> LENGTH: 393
<212> TYPE: DNA
<213> ORGANISM: Artificial Sequence
<220> FEATURE:
<223> OTHER INFORMATION: variable region of TRA specific for E5 epitope,
    TRAV17

<400> SEQUENCE: 60
atggaaactc tcctgggagt gtctttggtg attctatggc ttcaactggc tagggtgaac    60
agtcaacagg gagaagagga tcctcaggcc ttgagcatcc aggagggtga aaatgccacc   120
atgaactgca gttacaaaac tagtataaac aatttacagt ggtatagaca aaattcaggt   180
agaggccttg tccacctaat tttaatacgt tcaaatgaaa gagagaaaca cagtggaaga   240
ttaagagtca cgcttgacac ttccaagaaa agcagtt ggcgcaggaa ccattctgag agtcaagtcc tat                                393

<210> SEQ ID NO 61
<211> LENGTH: 393
<212> TYPE: DNA
<213> ORGANISM: Artificial Sequence
<220> FEATURE:
<223> OTHER INFORMATION: variable region of TRB specific for E5 epitope,
      TRBV6-5

<400> SEQUENCE: 61
atgagcatcg gcctcctgtg ctgtgcagcc ttgtctctcc tgtgggcagg tccagtgaat      60
gctggtgtca ctcagacccc aaaattccag gtcctgaaga caggacagag catgacactg     120
cagtgtgccc aggatatgaa ccatgaatac atgtcctggt atcgacaaga cccaggcatg     180
gggctgaggc tgattcatta ctcagttggt gctggtatca ctgaccaagg agaagtcccc     240
aatggctaca atgtctccag atcaaccaca gaggatttcc cgctcaggct gctgtcggct     300
gctccctccc agacatctgt gtacttctgt gccagcagtt accggcagca agagacccag     360
tacttcgggc caggcacgcg gctcctggtg ctc                                 393

<210> SEQ ID NO 62
<211> LENGTH: 402
<212> TYPE: DNA
<213> ORGANISM: Artificial Sequence
<220> FEATURE:
<223> OTHER INFORMATION: variable region of TRA specific for pp65
      epitope, TRAV17

<400> SEQUENCE: 62
atggaaactc tcctgggagt gtcattggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct acggttatcc ggatggatag cagctataaa     360
ttgatcttcg ggagtgggac cagactgctg gtcaggcctg at                       402

<210> SEQ ID NO 63
<211> LENGTH: 405
<212> TYPE: PRT
<213> ORGANISM: Artificial Sequence
<220> FEATURE:
<223> OTHER INFORMATION: variable region of TRB specific for pp65
      epitope, TRBV7-9

<400> SEQUENCE: 63

Ala Thr Gly Gly Gly Cys Ala Cys Cys Ala Gly Cys Cys Thr Cys Cys
1               5                   10                  15

Thr Cys Thr Gly Cys Thr Gly Gly Ala Thr Gly Cys Cys Cys Thr
            20                  25                  30

Gly Thr Gly Thr Cys Thr Cys Cys Thr Gly Gly Gly Gly Cys Ala
        35                  40                  45

Gly Ala Thr Cys Ala Cys Gly Cys Ala Gly Ala Thr Ala Cys Thr Gly
    50                  55                  60

Gly Ala Gly Thr Cys Thr Cys Cys Cys Ala Gly Gly Ala Cys Cys Cys
65                  70                  75                  80

```
Cys Ala Gly Ala Cys Ala Cys Ala Gly Ala Thr Cys Ala Cys Ala
                 85                  90                  95
Ala Ala Gly Ala Gly Gly Gly Ala Cys Ala Gly Ala Ala Thr Gly
            100                 105                 110
Thr Ala Ala Cys Thr Thr Thr Cys Ala Gly Gly Thr Gly Thr Gly Ala
            115                 120                 125
Thr Cys Cys Ala Ala Thr Thr Cys Thr Gly Ala Ala Cys Ala Cys
            130                 135                 140
Ala Ala Cys Cys Gly Cys Cys Thr Thr Thr Ala Thr Gly Gly Thr
145                 150                 155                 160
Ala Cys Cys Gly Ala Cys Ala Gly Ala Cys Cys Thr Gly Gly Gly
                165                 170                 175
Gly Cys Ala Gly Gly Gly Cys Cys Ala Gly Ala Gly Thr Thr Thr
                180                 185                 190
Cys Thr Gly Ala Cys Thr Thr Ala Cys Thr Thr Cys Cys Ala Gly Ala
                195                 200                 205
Ala Thr Gly Ala Ala Gly Cys Thr Cys Ala Ala Cys Thr Ala Gly Ala
            210                 215                 220
Ala Ala Ala Ala Thr Cys Ala Ala Gly Gly Cys Thr Gly Cys Thr Cys
225                 230                 235                 240
Ala Gly Thr Gly Ala Thr Cys Gly Gly Thr Thr Cys Thr Cys Thr Gly
                245                 250                 255
Cys Ala Gly Ala Gly Ala Gly Cys Cys Thr Ala Ala Gly Gly Gly
                260                 265                 270
Ala Thr Cys Thr Thr Thr Cys Thr Cys Cys Ala Cys Cys Thr Thr Gly
            275                 280                 285
Gly Ala Gly Ala Thr Cys Cys Ala Gly Cys Gly Cys Ala Cys Ala Gly
                290                 295                 300
Ala Gly Cys Ala Gly Gly Gly Gly Ala Cys Thr Cys Gly Gly Cys
305                 310                 315                 320
Cys Ala Thr Gly Thr Ala Thr Cys Thr Cys Thr Gly Cys Gly Cys Cys
                325                 330                 335
Ala Gly Cys Ala Gly Cys Thr Thr Ala Ala Thr Ala Gly Gly Gly Gly
            340                 345                 350
Thr Cys Ala Gly Cys Thr Cys Cys Thr Ala Cys Ala Ala Thr Gly Ala
            355                 360                 365
Gly Cys Ala Gly Thr Thr Cys Thr Thr Cys Gly Gly Gly Cys Cys Ala
            370                 375                 380
Gly Gly Gly Ala Cys Ala Cys Gly Gly Cys Thr Cys Ala Cys Cys Gly
385                 390                 395                 400
Thr Gly Cys Thr Ala
            405

<210> SEQ ID NO 64
<211> LENGTH: 5
<212> TYPE: PRT
<213> ORGANISM: Artificial Sequence
<220> FEATURE:
<223> OTHER INFORMATION: CDR1 of TRA specific for E5 epitope

<400> SEQUENCE: 64

Thr Ser Ile Asn Asn
1               5

<210> SEQ ID NO 65
<211> LENGTH: 7
```

```
<212> TYPE: PRT
<213> ORGANISM: Artificial Sequence
<220> FEATURE:
<223> OTHER INFORMATION: CDR2 of TRA specific for E5 epitope

<400> SEQUENCE: 65

Ile Arg Ser Asn Glu Arg Glu
1               5

<210> SEQ ID NO 66
<211> LENGTH: 5
<212> TYPE: PRT
<213> ORGANISM: Artificial Sequence
<220> FEATURE:
<223> OTHER INFORMATION: CDR1 of TRB specific for E5 epitope

<400> SEQUENCE: 66

Met Asn His Glu Tyr
1               5

<210> SEQ ID NO 67
<211> LENGTH: 6
<212> TYPE: PRT
<213> ORGANISM: Artificial Sequence
<220> FEATURE:
<223> OTHER INFORMATION: CDR2 of TRB specific for E5 epitope

<400> SEQUENCE: 67

Ser Val Gly Ala Gly Ile
1               5

<210> SEQ ID NO 68
<211> LENGTH: 5
<212> TYPE: PRT
<213> ORGANISM: Artificial Sequence
<220> FEATURE:
<223> OTHER INFORMATION: CDR1 of TRA specific for pp65 epitope

<400> SEQUENCE: 68

Thr Ser Ile Asn Asn
1               5

<210> SEQ ID NO 69
<211> LENGTH: 7
<212> TYPE: PRT
<213> ORGANISM: Artificial Sequence
<220> FEATURE:
<223> OTHER INFORMATION: CDR2 of TRA specific for pp65 epitope

<400> SEQUENCE: 69

Ile Arg Ser Asn Glu Arg Glu
1               5

<210> SEQ ID NO 70
<211> LENGTH: 5
<212> TYPE: PRT
<213> ORGANISM: Artificial Sequence
<220> FEATURE:
<223> OTHER INFORMATION: CDR1 of TRB specific for pp65 epitope

<400> SEQUENCE: 70

Ser Glu His Asn Arg
1               5

<210> SEQ ID NO 71
<211> LENGTH: 6
<212> TYPE: PRT
```

```
<213> ORGANISM: Artificial Sequence
<220> FEATURE:
<223> OTHER INFORMATION: CDR2 of TRB specific for pp65 epitope

<400> SEQUENCE: 71

Phe Gln Asn Glu Ala Gln
1               5
```